(12) United States Patent
Yonce

(10) Patent No.: US 6,496,721 B1
(45) Date of Patent: Dec. 17, 2002

(54) AUTOMATIC INPUT IMPEDANCE BALANCING FOR ELECTROCARDIOGRAM (ECG) SENSING APPLICATIONS

(75) Inventor: David J. Yonce, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/561,063

(22) Filed: Apr. 28, 2000

(51) Int. Cl.$^7$ ................................................. A61B 5/04
(52) U.S. Cl. ......................................................... 600/509
(58) Field of Search ........................... 600/509; 128/901, 128/902

(56) References Cited

U.S. PATENT DOCUMENTS

| | | | |
|---|---|---|---|
| 3,710,778 A | 1/1973 | Cornelius | 128/2 G |
| 3,991,747 A | 11/1976 | Stanly et al. | 128/2.06 R |
| 4,090,176 A | 5/1978 | Rodler | 340/189 M |
| 4,191,195 A | 3/1980 | Miller | 128/696 |
| 4,467,813 A | 8/1984 | Schomburg | 128/702 |
| 4,779,617 A | 10/1988 | Whigham | 128/419 P |
| 5,010,887 A | 4/1991 | Thornander | 128/696 |
| 5,139,028 A | 8/1992 | Steinhaus et al. | 128/697 |
| 5,201,808 A | 4/1993 | Steinhaus et al. | 128/419 PG |
| 5,203,326 A | 4/1993 | Collins | 128/419 PG |
| 5,230,336 A | 7/1993 | Fain | 607/7 |
| 5,251,621 A | 10/1993 | Collins | 607/4 |
| 5,264,798 A | 11/1993 | Bey, Jr. et al. | 324/725 |
| 5,435,316 A | 7/1995 | Kruse | 128/697 |
| 5,615,687 A * | 4/1997 | Pritchard | |
| 5,749,869 A | 5/1998 | Lindenmeier et al. | 606/34 |
| 5,766,230 A | 6/1998 | Routh et al. | 607/27 |
| 5,792,194 A | 8/1998 | Morra | 607/17 |
| 5,837,001 A | 11/1998 | Mackey | 607/102 |
| 5,862,803 A | 1/1999 | Besson et al. | 128/696 |
| 5,902,249 A | 5/1999 | Lyster | 600/509 |
| 6,208,888 B1 | 3/2001 | Yonce | 600/509 |

FOREIGN PATENT DOCUMENTS

| | | | |
|---|---|---|---|
| EP | 0568199 | 3/1993 | G05B/19/00 |
| EP | 0617917 | 3/1993 | A61B/5/0428 |

OTHER PUBLICATIONS

Bey, P., et al., "Autonulling ac bridge for accurate measurement of small impedance variations uisng MOS components", *Review of Scientific Instruments*, vol. 62, No. 12, pp. 3082–3088 (Dec. 1991).

Bey, P., et al., "Stability Analysis of an Autonulling AV Bridge for USe with Silicon–Based Sensors", *IEEE Transactions on Circuits and Systems–I: Fundamental Theory and Applications*, vol. 41, No. 3, pp. 210–219 (Mar. 1994).

* cited by examiner

Primary Examiner—Scott M. Getzow
(74) Attorney, Agent, or Firm—Schwegman, Lundberg, Woessner & Kluth, P.A.

(57) ABSTRACT

A voltage sensing system includes input impedance balancing for electrocardiogram (ECG) sensing or other applications, providing immunity to common-mode noise signals while capable of use with two electrodes. Signals are received at first and second electrodes having associated impedances. An impedance circuit includes a feedback controller that adjusts an effective impedance associated with the second electrode based on a difference signal, a common mode signal, a phase-shifted (e.g., quadrature common mode) signal, and an impedance associated with the first electrode. As a result, signals associated with each electrode undergo a similar degree of gain/attenuation and/or phase-shift. This reduces common mode noise and enhances the signal-to-noise characteristics of a desired ECG or other output signal, without requiring the use of more than two electrodes.

38 Claims, 23 Drawing Sheets

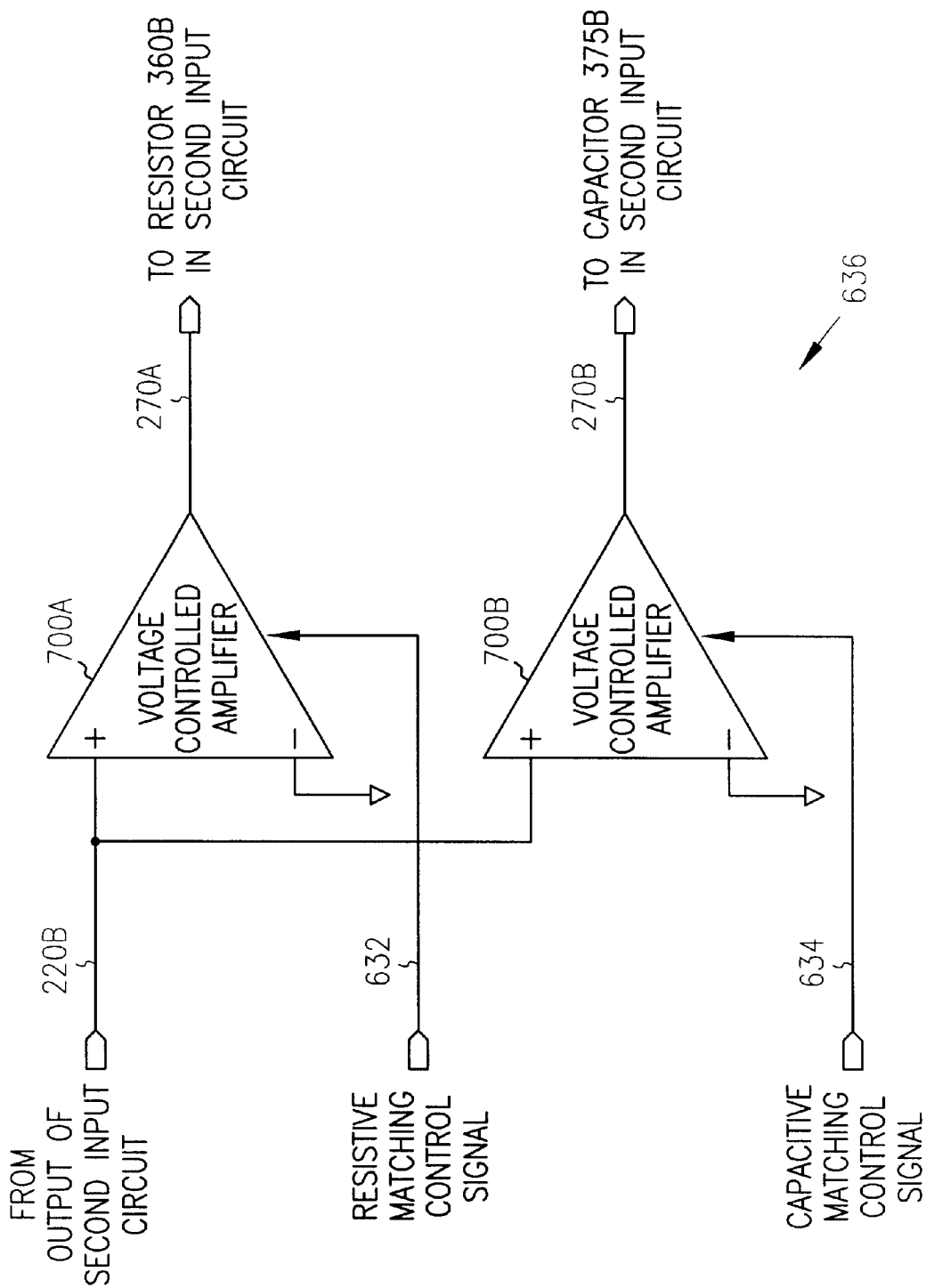

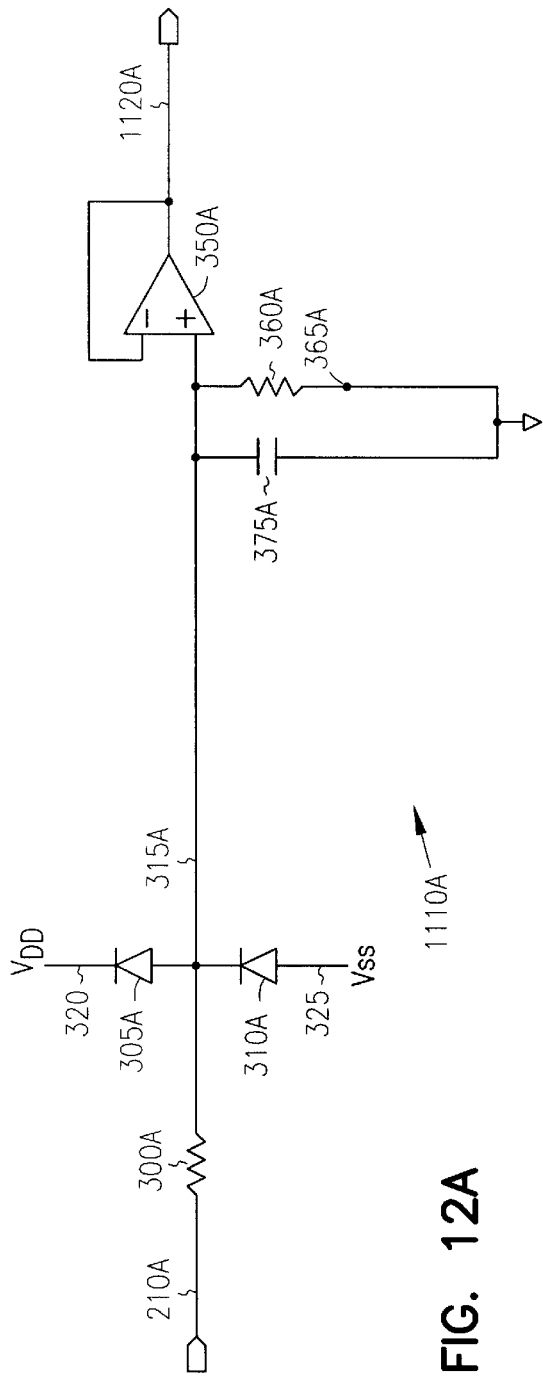
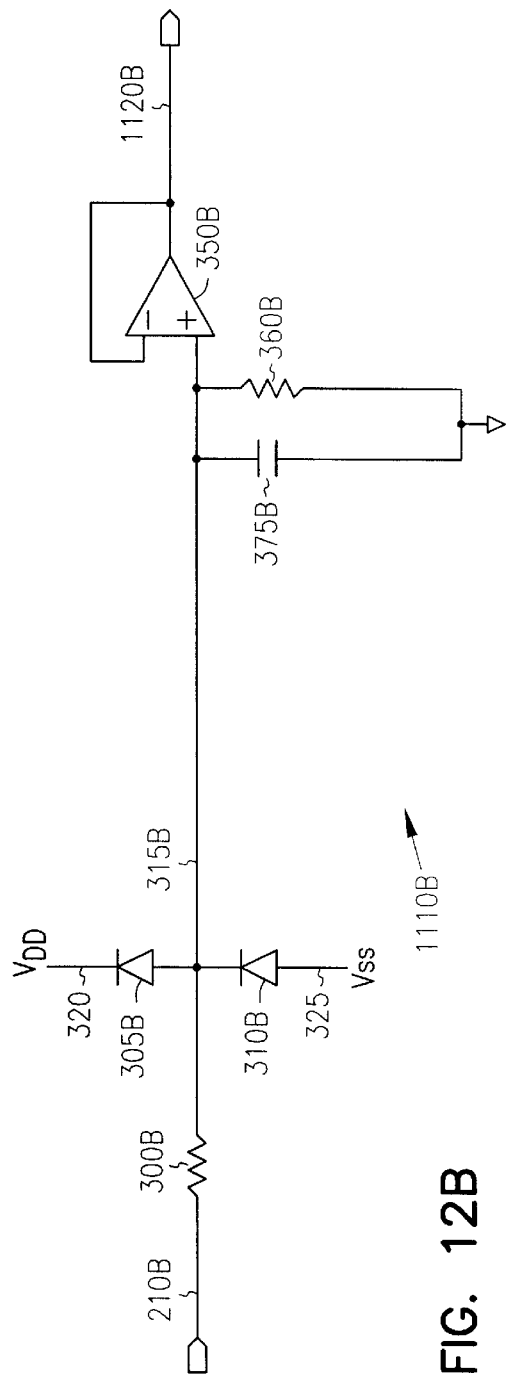
FIG. 12A
FIG. 12B

AUTOMATIC INPUT IMPEDANCE BALANCING FOR ELECTROCARDIOGRAM (ECG) SENSING APPLICATIONS

CROSS REFERENCE TO RELATED APPLICATIONS

This application is related to the following co-pending, commonly assigned U.S. patent application: "VOLTAGE SENSING SYSTEM WITH INPUT IMPEDANCE BALANCING FOR ELECTROCARDIOGRAM (ECG) SENSING APPLICATIONS", Ser. No. 09/243,265, filed on Feb. 3, 1999, the specification of which is herein incorporated by reference.

TECHNICAL FIELD

This invention relates generally to a voltage sensing system and particularly, but not by way of limitation, to a voltage sensing system with input impedance balancing for electrocardiogram (ECG) sensing applications.

BACKGROUND

When functioning properly, the human heart maintains its own intrinsic rhythm, and is capable of pumping adequate blood throughout the body's circulatory system. The body's autonomous nervous system generates intrinsic electrical heart activity signals that are conducted to atrial and ventricular heart chambers on the left and right sides of the heart. The electrical heart activity signals trigger resulting heart contractions that pump blood.

The intrinsic electrical heart activity signals can be monitored to provide an electrocardiogram (ECG) signal to a physician, clinician, diagnostician, or researcher to obtain information about heart function. In one such technique, a first external skin patch electrodes is adhesively affixed to the patient's right arm. A second external skin patch electrode is adhesively affixed to the patient's left arm. An instrumentation amplifier is used to detect the electrical heart activity signals at the first and second electrodes. The instrumentation amplifier outputs an ECG signal based on the difference of the signals at the first and second electrodes.

If no further electrodes are used, the ECG signal obtained between the first and second electrodes is typically severely degraded by common-mode (CM) noise signals, such as 60 Hertz or other environmental noise signals that are present at both of the first and second electrodes. Common-mode noise problems generally result even if a high-quality instrumentation amplifier is used. Skin-electrode interface impedance differences between the first and second electrodes contribute to such common-mode noise problems. Differences in skin-electrode interface impedances result from differences in body morphology, adhesion of the electrode, perspiration by the patient, etc. Because of the high input-impedance of the instrumentation amplifier, even small differences in the skin-electrode impedance (e.g., 10 kilo-ohms) can result in a common-mode noise signal amplitude that exceeds the amplitude of the desired ECG signal.

One technique of reducing the common-mode noise signal is to attach a third electrode, such as at the patient's right leg, for use in a feedback arrangement. The third electrode is driven by an offsetting common-mode signal to cancel a portion of the unwanted common-mode noise signal. However, this technique is inconvenient for the physician, because it requires attachment of the third electrode to the patient. This increases the complexity of the medical procedure. In a medical emergency, for example, such increased complexity is highly undesirable. Thus, there is a need for improved ECG measurement techniques providing adequate common-mode noise immunity without relying exclusively on attaching additional electrodes to the patient.

SUMMARY

The present system provides, among other things, a voltage sensing system with input impedance balancing for electrocardiogram (ECG) sensing or other applications. The present system allows sensing of ECG or other input voltage signals and reduces sensing of unwanted common-mode noise signals. The present system is capable of use with two electrodes, while still providing good signal-to-noise characteristics.

According to one aspect of the present system, signals are received at first and second electrodes or terminals, each having an impedance associated therewith. An effective impedance associated with the second electrode is adjusted based on an effective impedance associated with the first electrode. In one embodiment, an impedance circuit adjusts the effective impedance associated with the second electrode based on difference and common mode signals obtained from signals at the first and second electrodes. As a result, signals associated with each electrode undergo a similar degree of gain/attenuation and/or phase-shift. This reduces common mode noise and enhances the signal-to-noise characteristics of a desired ECG or other output signal, without requiring the use of more than two electrodes. Thus, in an ECG signal acquisition application, the present system enhances the noise immunity of the ECG signal without increasing the complexity of the associated medical procedure. Other aspects of the invention will be apparent on reading the following detailed description of the invention and viewing the drawings that form a part thereof.

According to another aspect of the present system, buffer amplifiers are added to the front end of the input circuitry, instead of compensating skin-electrode impedance mismatches at the input, to circumvent the problems associated with high capacitance cables,. This allows the ECG system to always present constant input impedance at the patient electrodes. This also permits higher capacitance values on the input without swamping out the impedance balancing range.

Another illustrative embodiment includes a switch to control flow of right leg (RL) signal (coming from the third electrode) into ECG cable to selectively turn-off the RL signal, when the RL electrode is not in use, to prevent the RL signal from entering the ECG cable for optimum performance (the standard industry ECG cable incorporates 4 input cables, and one RL output cable with a single connector connecting to the ECG system). Generally there is no means available to disconnect the RL cable, when the right-leg drive is not in use).

Another illustrative embodiment includes an automatic gain control module between the common-mode input and the impedance circuit to maintain a constant transient response time over a wide range of input noise levels.

Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views.

FIG. 7 is a schematic diagram illustrating generally one embodiment of an impedance control sub-circuit.

FIG. 12A is a schematic diagram illustrating generally another embodiment of a first input circuit.

FIG. 12B is a schematic diagram illustrating generally another embodiment of a second input circuit.

DETAILED DESCRIPTION

Figure 1:
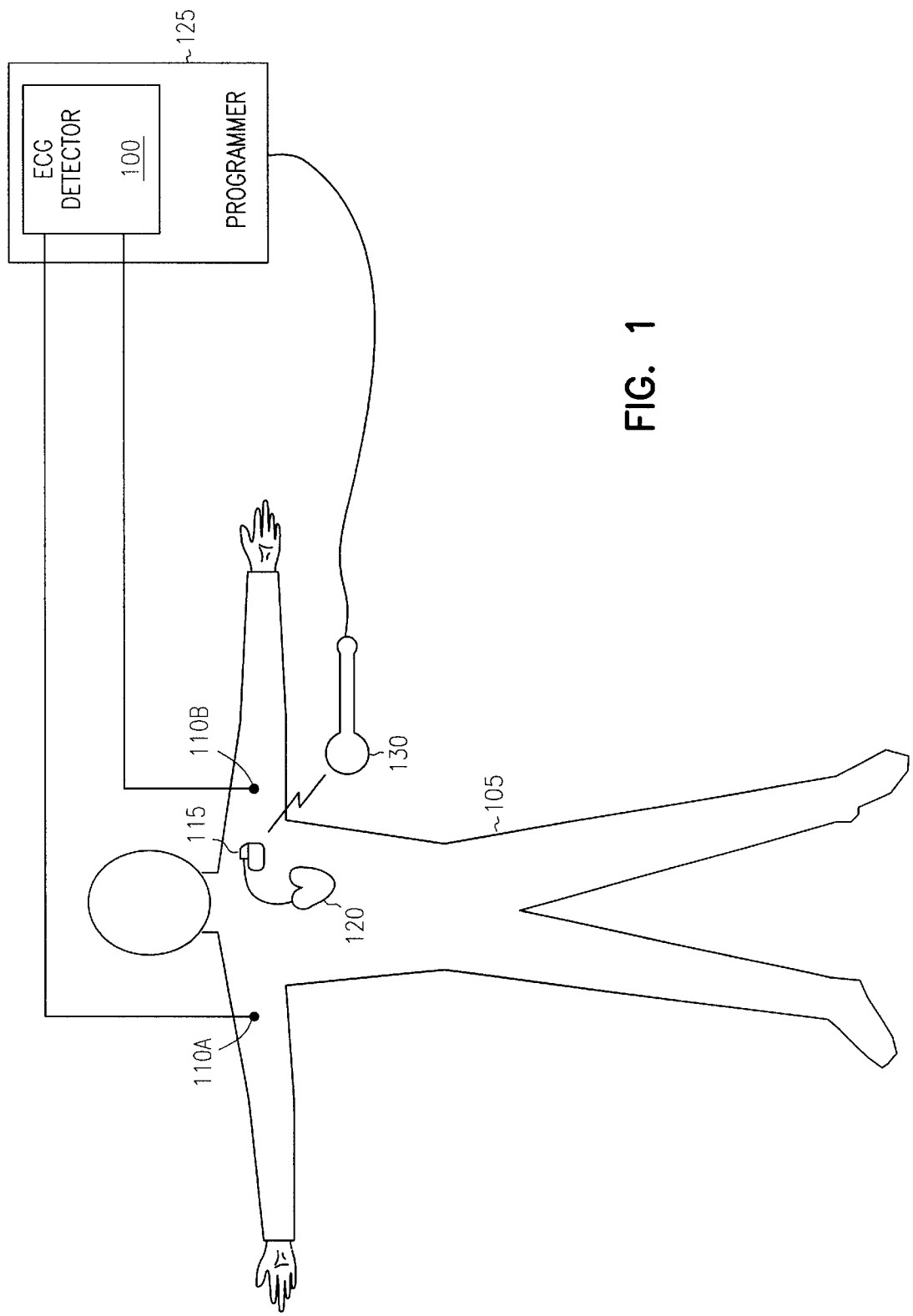
FIG. 1 is a schematic/block diagram illustrating generally one embodiment of portions of a voltage sensing system and an environment in which it is used.

In the following detailed description, reference is made to the accompanying drawings, which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views.

In this document, the term gain is understood to refer to both gains greater than one and gains that are less than or equal to one (i.e., the term gain includes attenuation). Similarly, the term amplification is understood to include both gains greater than one and gains that are less than or equal to one. Furthermore, amplification refers to amplification of differential mode signals and/or amplification of common mode signals. Amplifier is understood to incorporate the above understanding of amplification.

General System Overview

This document describes, among other things, a voltage sensing system with input impedance balancing for electrocardiogram (ECG) sensing or other applications. The present system allows sensing of ECG or other input voltage signals and reduces sensing of unwanted common-mode noise signals. The present system does not require the use of more than two electrodes. However, it is understood that more than two electrodes can be used in the present system such as, for example, to further improve its signal-to-noise ratio.

Embodiment #1

FIG. 1 is a schematic/block diagram illustrating generally, by way of example, but not by way of limitation, one embodiment of portions of the present voltage sensing system and an environment in which it is used. In FIG. 1, a voltage sensing system includes, for example, an ECG detector 100. The ECG detector 100 is coupled, via lead wires or otherwise, to input terminals, such as first and second electrodes 110A–B located at or communicatively coupled to a living organism, such as human or other patient 105. In one embodiment, first electrode 110A is disposed at or near a right arm of patient 105 and second electrode 110B is disposed at or near a left arm of patient 105. First and second electrodes 110A–B are optionally skin patch electrodes that are affixed to the patient's skin, such as using a conductive adhesive or otherwise. Although the embodiment illustrated in FIG. 1 utilizes external electrodes 110A–B, it is understood that other embodiments of the present voltage sensing system use electrodes that are implanted in patient 105.

In one embodiment, ECG detector 100 is optionally included in a cardiac rhythm management system. In one such example, the cardiac rhythm management system also includes an implanted cardiac rhythm management device 115, such as a pacer, a defibrillator, or a pacer/defibrillator. The implanted device 115 is coupled to heart 120, such as by one or more lead-wires or otherwise, for delivering cardiac rhythm management therapy (e.g., electrical pulses or defibrillation countershocks). In one embodiment, the cardiac rhythm management system further includes an external programmer 125. A communication device, such as telemetry device 130, communicatively couples external programmer 125 to implanted device 115. Programmer 125 includes ECG detector 100.

Figure 2:
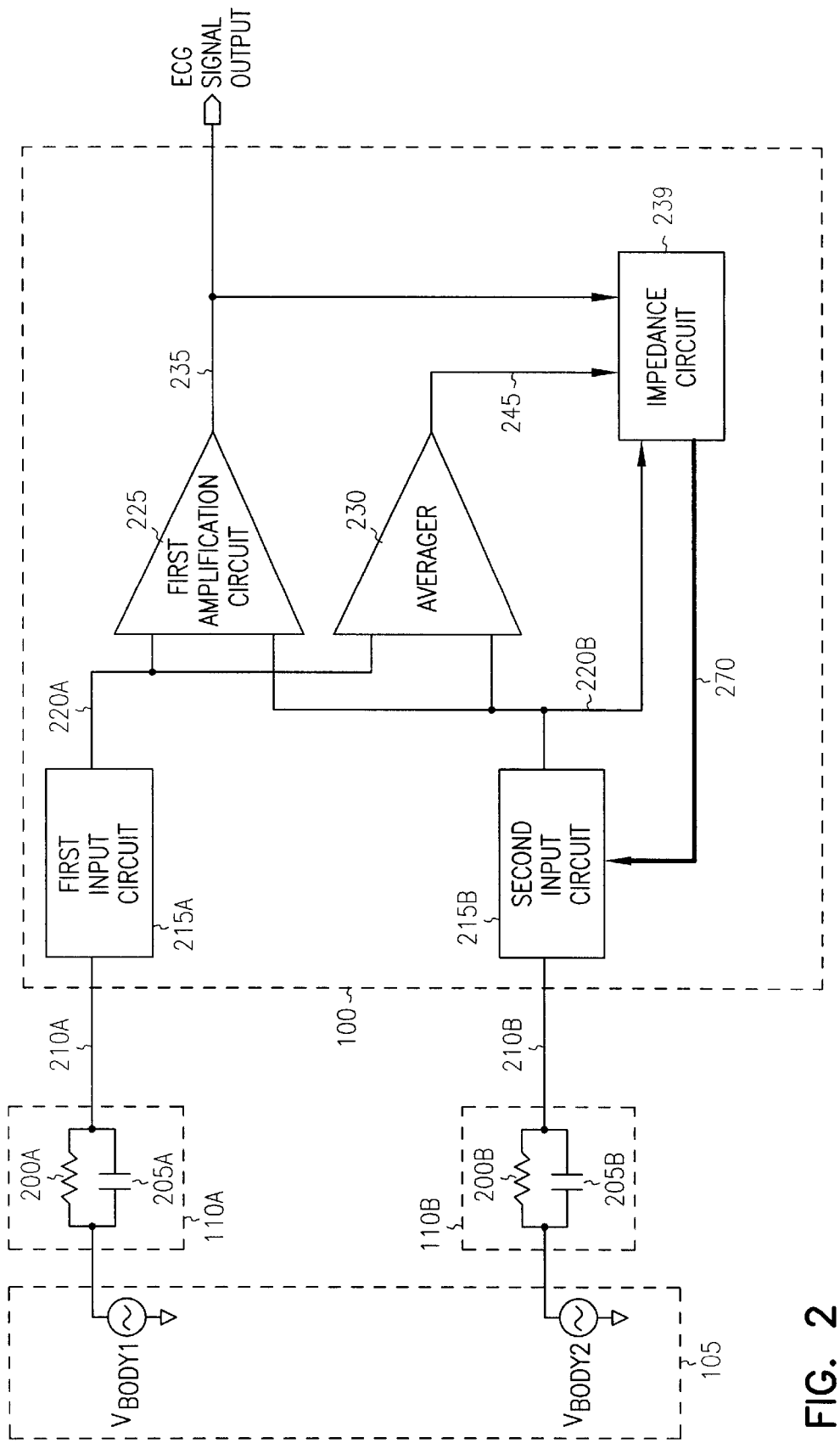
FIG. 2 is a schematic/block diagram that illustrates generally one embodiment of portions of a voltage sensing system, such as an ECG detector, and an environment in which it is used.

FIG. 2 is a schematic/block diagram that illustrates generally, by way of example, but not by way of limitation, one embodiment of portions of a voltage sensing system, such as ECG detector 100, and an environment in which it is used. In FIG. 2, body voltages including an electrical heart activity signal are received at first and second electrodes 110A–B, which are modeled schematically. First electrode 110A has an effective skin-electrode impedance modeled by resistor 200A in parallel with capacitor 205A. Similarly, second electrode 110A has an effective skin-electrode impedance modeled by resistor 200B in parallel with capacitor 205B. Electrodes 110A–B are coupled, at respective nodes 210A–B, to respective first and second input circuits 215A–B associated with ECG detector 100. Input circuits 215A–B provide outputs at respective nodes 220A–B. Nodes 220A–B are each coupled to both of first amplification circuit 225 and averager 230.

An output of first amplification circuit 225, at node 235, provides an ECG signal output and is coupled to impedance circuit 239. An output of averager 230, at node 245, provides a common mode signal that is coupled to impedance circuit 239. At least one output of impedance circuit 239 is coupled to second input circuit 215B for controlling its impedance to reduce the common mode noise signal at the ECG signal output node 235.

As discussed above, the effective impedances of first electrode 110A and second electrode 110B may be different. This causes the amount of signal attenuation from the input of electrode 110A to node 210A to be different from the amount of signal attenuation from the input of electrode 110B to node 210B. According to prior art techniques, this resulted in an unwanted common-mode noise signal amplitude, at node 235, that exceeds the desired ECG signal amplitude at node 235. According to one aspect of the present system, however, impedance circuit 239 substantially offsets, corrects, or compensates for effects of the impedance mismatch between electrodes 110A–B. As a result, the effective signal attenuation from the input of electrode 110A to node 220A is approximately equal to the effective signal attenuation from the input of electrode 110B to node 210B. This, in turn, decreases the common-mode noise at ECG signal output node 235, such that the desired ECG signal is more readily discernable at node 235.

Examples of Input Circuits

Figure 3A:
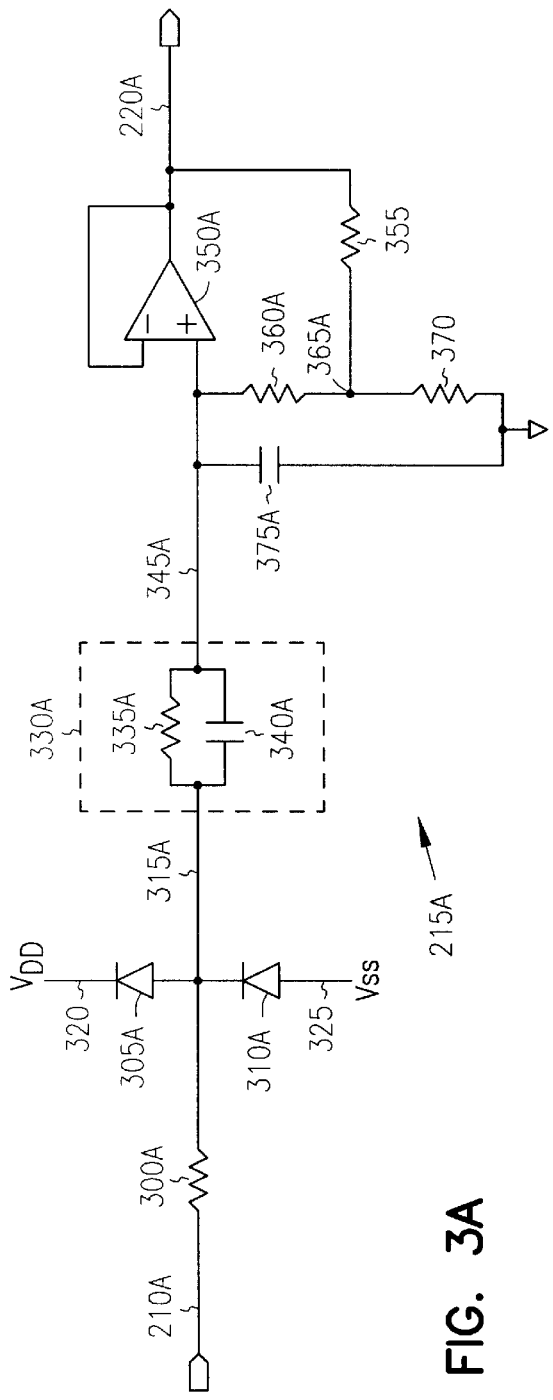
FIG. 3A is a schematic diagram illustrating generally one embodiment of a first input circuit.

FIG. 3A is a schematic diagram illustrating generally, by way of example, but not by way of limitation, one embodiment of first input circuit 215A. The input signal from first electrode 110A is received at node 210A through series protection as resistor 300A. Resistor 300A limits a current received by subsequent circuits when high energy is received, such as from electrostatic discharges (ESD) or from the delivery of a defibrillation counter-shock to heart 120. This protects such circuits against possible damage. Similarly, protection diodes 305A and 310A clamp the voltage at node 315A, such that it does not exceed the positive power supply voltage, $V_{DD}$, at node 320, by more than a diode voltage, and such that the voltage at node 315A does not fall below the negative power supply voltage, $V_{SS}$, at node 325, by more than a diode voltage.

In one embodiment, input circuit 215A also includes a phase shifter 330A. In one example, phase shifter 330A includes a series phase lead network formed by resistor 335A in parallel with capacitor 340A. An output of phase shifter 330A is coupled, at node 345A, to a positive input of a buffer such as that of buffer amplifier 350A. An output, at node 220A, of amplifier 350A is fed back to its negative input. The output at node 220A of amplifier 350A is also fed back to its positive input through feedback resistor 355 and input resistor 360A. An intermediate node 365A, between series-connected feedback resistor 355 and input resistor 360A, is coupled to a stable reference voltage, such as a ground node, through resistor 370. Input capacitor 375A is coupled between the positive input, at node 345A, of amplifier 350A, and the ground node.

Amplifier 350A and the network of resistors 355, 360A, and 370 form an impedance bootstrap circuit that effectively increases the effective impedance of input resistor 360A, as seen at node 345A, as compared what such impedance would be if resistor 360A directly coupled node 345A to the ground node. The impedance bootstrap circuit operates such that an increase in voltage at node 345A results in an increase in voltage at nodes 220A and 365A. This reduces the voltage across resistor 360A, which, in turn, reduces the current through resistor 360A. Because the resulting current through resistor 360A, in response to a given change in voltage at node 345A, is less than it would be if resistor 360A directly coupled node 345A to ground, Ohm's Law indicates that the effective impedance seen at node 345A is increased. Similarly, a decrease in voltage at node 345A results in a decrease in voltage at nodes 220A and 365A which, in turn, also reduces the current through resistor 360A, thereby increasing the effective resistance of resistor 360A as seen at node 345A.

Figure 4A:
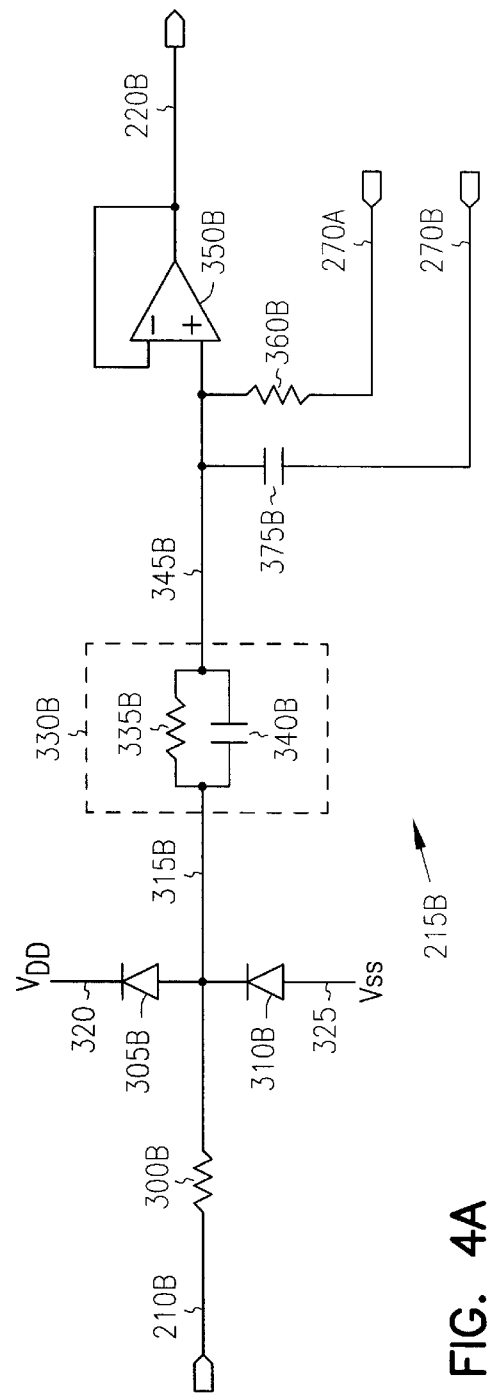
FIG. 4A is a schematic diagram illustrating generally one embodiment of a second input circuit.

FIG. 4A is a schematic diagram illustrating generally, by way of example, but not by way of limitation one embodiment of second input circuit 215B. As illustrated in FIG. 4A, second input circuit 215B is similar to first input circuit 215A. Operation of correspondingly numbered elements (but with a different suffix letter "B") is as described with respect to FIG. 3A. In FIG. 4A, however, input resistor 360B couples a signal received at node 270A, from impedance circuit 239, to the positive input, at node 345B, of a buffer, such as buffer amplifier 350B. Similarly, input capacitor 375B couples a signal received at node 270B, from impedance circuit 239, to the positive input, at node 345B, of buffer amplifier 350B.

FIG. 4A illustrates resistor 360B and capacitor 375B as being part of second input circuit 215B, for convenience of illustrating similarities and differences between first and second input circuits 215A–B. It is understood, however, that resistor 360B and capacitor 375B are alternatively regarded as being part of impedance circuit 239 rather than as being part of second input circuit 215B, and could alternatively be illustrated therewith.

In operation, the voltages at nodes 270A–B are adjusted by impedance circuit 239 (analogous to operation of the impedance bootstrap circuit described above with respect to FIG. 3A) to vary the effective impedance of resistor 360B and capacitor 375B such that a gain/attenuation between first electrode 110A and node 345A is approximately or substantially equal to a gain/attenuation between second electrode 110B and corresponding node 345B. In one embodiment, this results in an attenuation between first electrode 110A and node 220A that is approximately or substantially matched to an attenuation between second electrode 110B and corresponding node 220B.

By increasing the voltage at node 270A, relative to the voltage at node 345B, the effective resistance of input resistor 360B is increased. By decreasing the voltage at node 270A, relative to the voltage at node 345B, the effective resistance of input resistor 360B is decreased. According to one aspect of the present system, the voltage at input node 270A is controlled by impedance circuit 239 such that the effective resistance of input resistor 360B matches a resistive component of the effective impedance seen at node 345A of first input circuit 215A (when the resistor 200A of first electrode 110A is approximately equal to the resistor 200B of second electrode 110B and the capacitor 205A of first electrode 110A is approximately equal to the capacitor 205B of second electrode 110B).

By decreasing the voltage at node 270B, relative to the voltage at node 345B, the effective capacitance of input capacitor 375B is increased. By increasing the voltage at node 270B, relative to the voltage at node 345B, the effective capacitance of input capacitor 375B is decreased. According to one aspect of the present system, the voltage at input node 270B is controlled by impedance circuit 239 such that the effective capacitance of input capacitor 375B matches the reactive (e.g., capacitive) component of the effective impedance seen at node 345A of first input circuit 215A (when the resistor 200A of first electrode 110A is approximately equal to the resistor 200B of second electrode 110B and the capacitor 205A of first electrode 110A is approximately equal to the capacitor 205B of second electrode 110B).

Figure 3B:
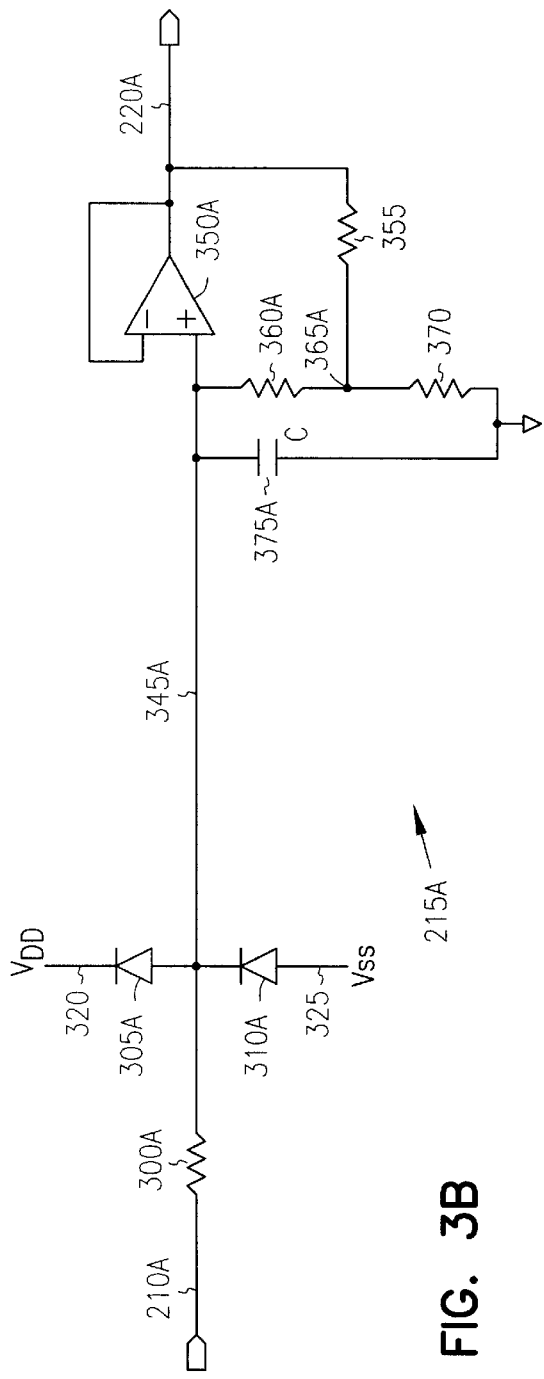
FIG. 3B is a schematic diagram illustrating generally another embodiment of a first input circuit.
Figure 4B:
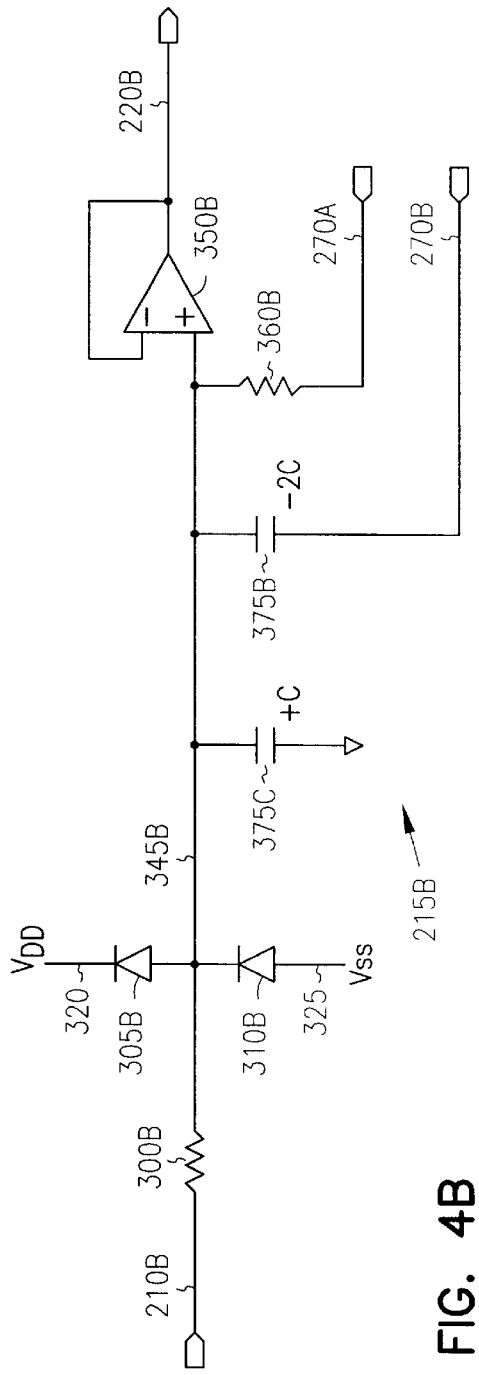
FIG. 4B is a schematic diagram illustrating generally another embodiment of a second input circuit.

The system is described above as including phase-lead networks 330A and 330B to accommodate a fall range of phase lags introduced by impedance circuit 239, resistor 360B, and capacitor 375B. Alternatively, phase lead networks 330A and 330B are omitted, and a negative impedance circuit is used in place of at least one of resistor 360B and capacitor 375B, as illustrated in FIGS. 3B and 4B by way of example, but not by way of limitation. In FIG. 4B, for example, an additional capacitor 375C is included, and capacitor 375B is implemented as a negative capacitance circuit. In this embodiment, capacitors 375A and 375C each have an approximately equal nominal capacitance value ("C"), and negative capacitor circuit 375B has a nominal capacitance value of –2C. Alternatively, capacitor 375A has a nominal capacitance value C, capacitor 375B has a nominal capacitance value 2C, and capacitor 375C is implemented as a negative capacitance network having a capacitance value of approximately –C.

Examples of Differential Amplifier, Averager, and Phase-Shifter

Figure 5A:
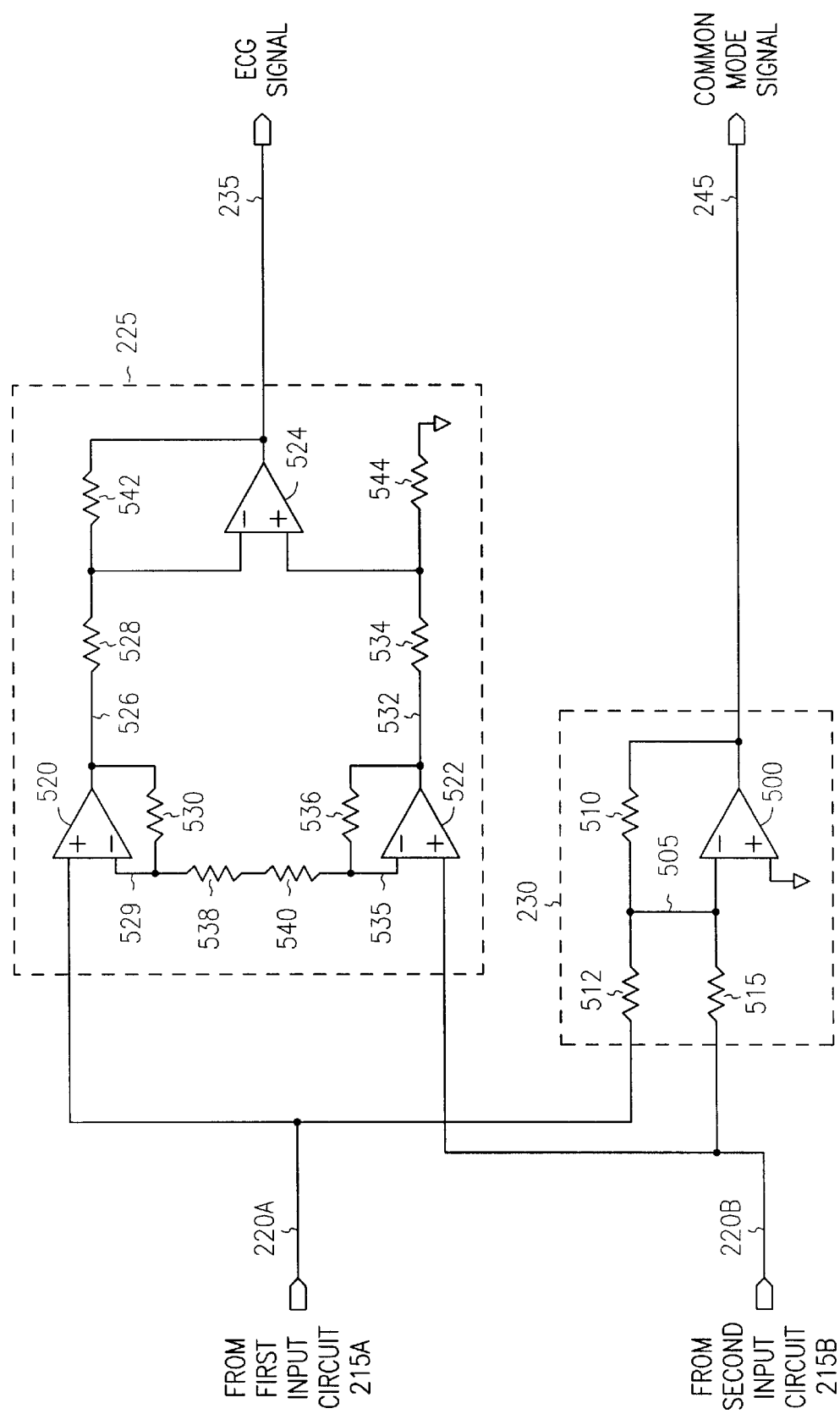
FIG. 5A is a schematic diagram illustrating generally one embodiment of a configuration of a first amplification circuit and an averager.

FIG. 5A is a schematic diagram illustrating generally, by way of example, but not by way of limitation, one embodiment of a configuration of first amplification circuit 225 and averager 230, such as illustrated in FIG. 2. In one embodiment, as illustrated in FIG. 5A, first amplification circuit 225 includes a differential input, single-ended output amplifier, such as an off-the-shelf or other instrumentation amplifier. First amplification circuit 225 receives input signals at nodes 220A–B from first and second input circuits 215A–B, respectively, and outputs an ECG signal at node 235.

In this embodiment, averager 230 includes a differential input, single-ended output operational amplifier 500. Amplifier 500 includes a positive input that is coupled to a ground node and an output, at node 245, that provides a common mode voltage of the signals at nodes 220A and 220B. The common mode signal at the node 245 is fed back to the inverting input, at node 505, of amplifier 500, such as through feedback resistor 510. The inverting input of amplifier 500, at node 505, is coupled via first input resistor 512 to receive a signal, at node 220A, from first input circuit 215A. The inverting input of amplifier 500, at node 505, is also coupled via second input resistor 515 to receive a signal, at node 220B, from second input circuit 215B. In an alternate embodiment, averager 230 includes a passive network (i.e., without using operational amplifier 500) for averaging the signals at nodes 220A–B.

In this embodiment, first amplifier 225 is configured as an instrumentation amplifier, which includes first operational amplifier 520, second operational amplifier 522 and third operational amplifier 524, each having differential inputs and a single-ended output. A non-inverting input of first operational amplifier 520 is coupled to first input circuit 215A at node 220A. The output, at node 526, of first operational amplifier 520 is fed to the inverting input of third operational amplifier 524 through resistor 528, and is also fed back through resistor 530 to the inverting input, at node 529, of first operational amplifier 520. A non-inverting input of second operational amplifier 522 is coupled to second input circuit 215B at node 220B. The output, at node 532, of second operational amplifier 522 is fed to the non-inverting input of third operational amplifier 524 through resistor 534, and is also fed back to the inverting input, at node 535, of second operational amplifier 522 through resistor 536. The inverting input node 529 of first operational amplifier 520 is coupled to the inverting input node 535 of second operational amplifier 522 through series-coupled resistors 538 and 540. The output of third operational amplifier 524 provides the ECG signal at node 235, and is coupled back to the inverting input of third operational amplifier through resistor 542. The non-inverting input of third operational amplifier 524 is coupled to a ground node through resistor 544.

Figure 5B:
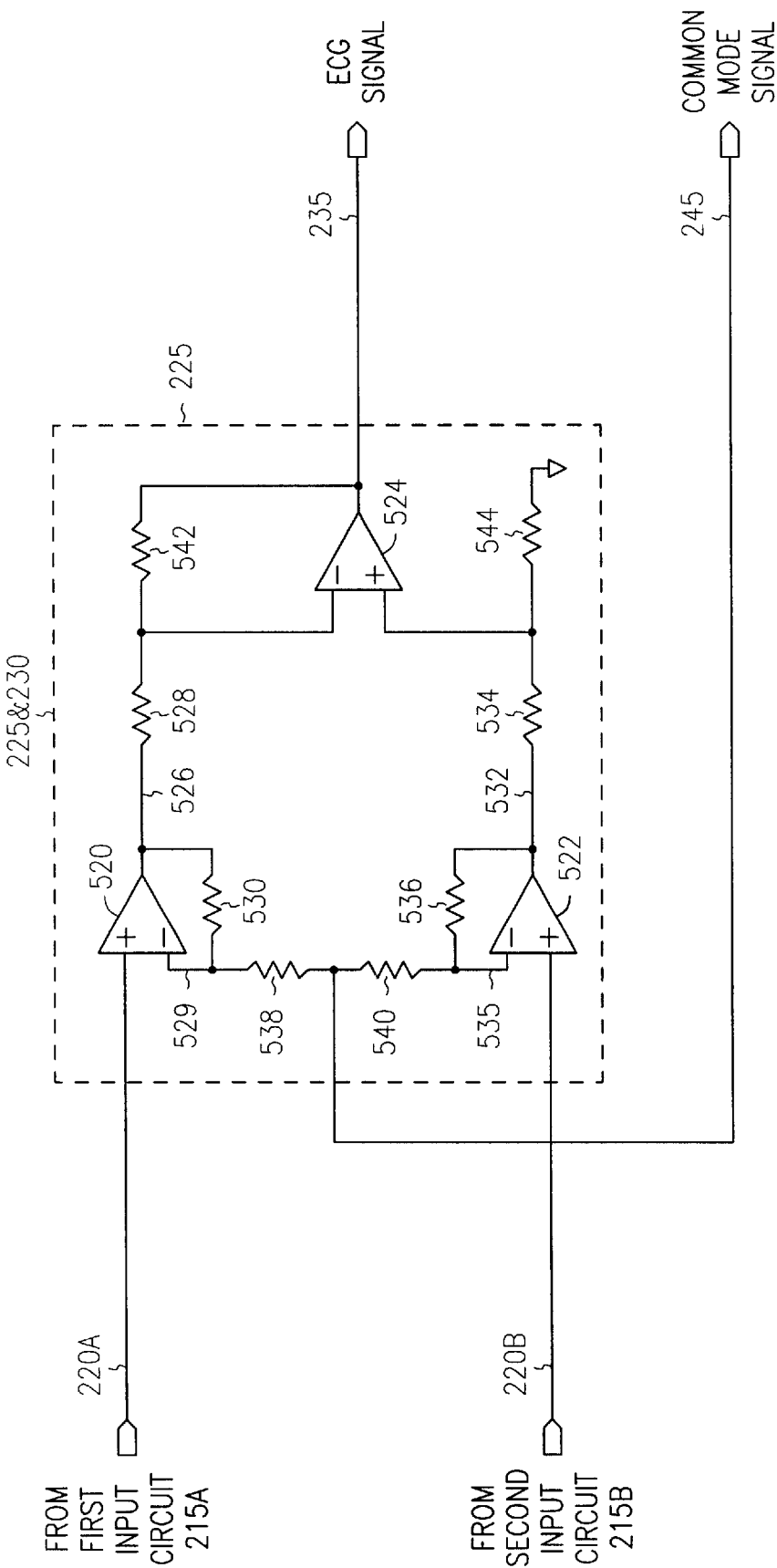
FIG. 5B is a schematic diagram illustrating generally one embodiment of a merged first amplification circuit and averager.

FIG. 5B is a schematic diagram illustrating generally, by way of example, but not by way of limitation, one embodiment of a configuration of a merged first amplification circuit 225 and averager 230. In this embodiment, a single instrumentation amplifier 225 is used, and the common mode-signal at node 245 is provided by the common mode output of the instrumentation amplifier taken between resistors 538 and 540.

Example Impedance Circuit

Figure 6A:
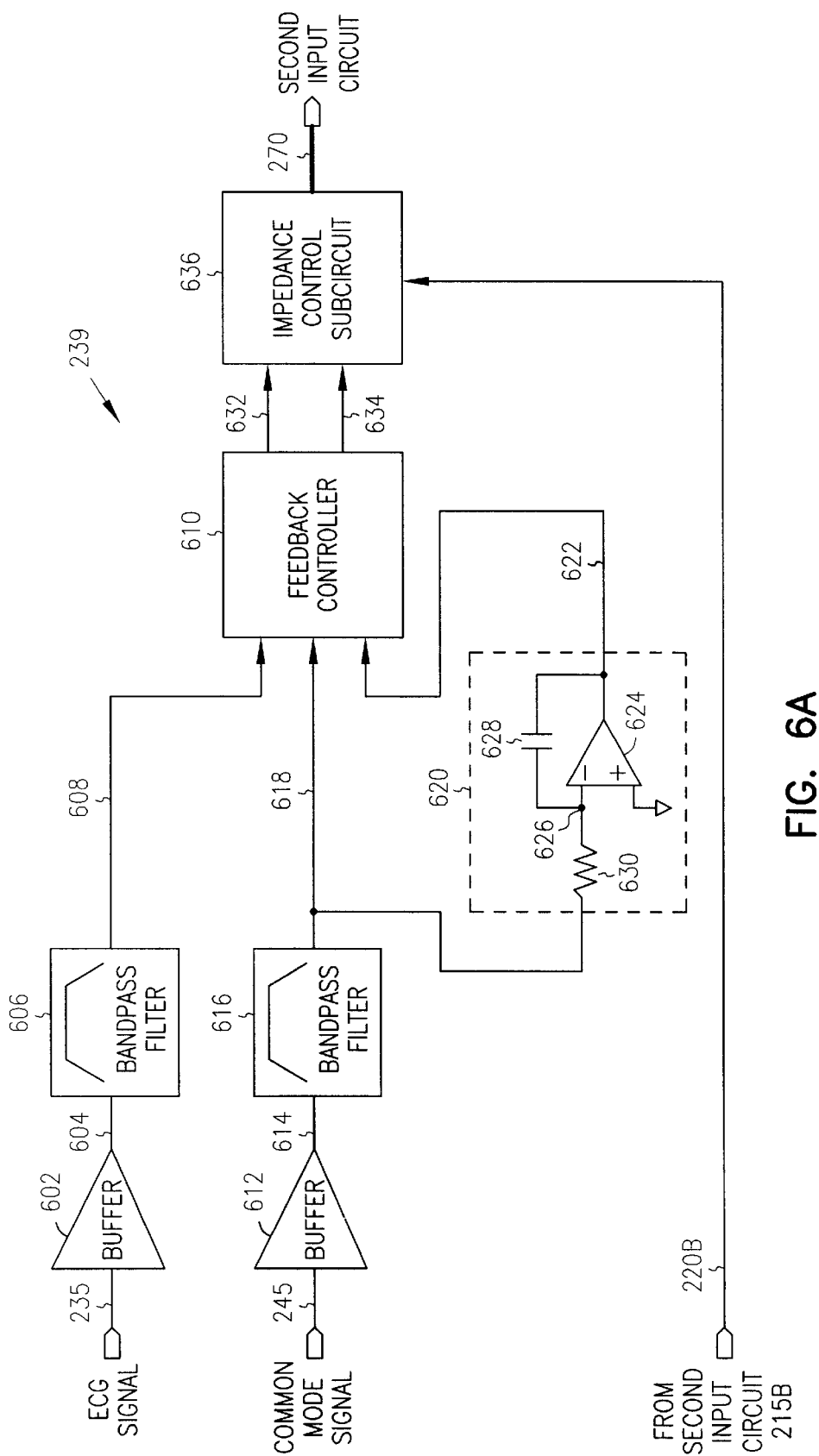
FIG. 6A is a schematic/block diagram illustrating generally one embodiment of an impedance circuit.

FIG. 6A is a schematic/block diagram illustrating generally, by way of example, but not by way of limitation, one embodiment of impedance circuit 239. Impedance circuit 239 receives the ECG signal, at node 235, the common mode signal, at node 245, and the output, at node 220B, of second input circuit 215B. The ECG signal at node 235 is amplified at buffer 602, which provides an output at node 604 that is then filtered by filter 606, which, in one embodiment, is a band-pass filter that attenuates frequencies outside the range of approximately 6–600 Hz (e.g., single pole roll-off frequencies). This, in turn, provides a filtered ECG signal output at node 608 to feedback controller 610. In one alternate embodiment, buffer 602 and filter 606 are combined. In another alternate embodiment, filter 606 is a highpass filter.

The common mode signal at node 245 is amplified at buffer 612, which provides an output at node 614 that is then filtered by filter 616, which, in one embodiment, is a bandpass filter that attenuates frequencies outside the range of approximately 6–600 Hz. This, in turn, provides a filtered common mode signal output at node 618 to feedback controller 610. In one alternate embodiment, buffer 612 and filter 616 are combined. In another alternate embodiment, filter 616 is a highpass filter.

The filtered common mode signal output at node 618 is also received by phase-shifter 620, which provides a filtered phase-shifted common mode signal output at node 622 to feedback controller 610. In one embodiment, phase-shifter 620 includes an integrator circuit that includes differential input, single-ended output operational amplifier 624. Amplifier 624 has a positive input, which is coupled to ground, and an output at node 622 that is fed back to its inverting input, at node 626, through a feedback capacitor 628. The inverting input of amplifier 624 is also coupled, via input resistor 630, to receive the filtered common mode output signal, at node 618, from the output of filter 616. Phase-shifter 620 provides a filtered phase-shifted common mode output signal, at node 622 (which, in one embodiment, is approximately 90 degrees out of phase with the common mode signal at node 245 and is also referred to as a filtered quadrature common mode signal). In an alternative embodiment, phase-shifter 620 is configured as a differentiator, rather than as an integrator (i.e., resistor 630 is configured in the feedback path around amplifier 624 and capacitor 628 is interposed between nodes 618 and 626).

Based on the filtered ECG signal at node 608, the filtered common mode signal at node 618, and the filtered quadrature common mode signal at node 622, feedback controller 610 provides a resistive matching control signal, at node 632, and a capacitive matching control signal, at node 634, to impedance control subcircuit 636. Impedance control subcircuit 636 also receives the output signal, at node, 220B, from second input circuit 215B. Based on these input signals, impedance control subcircuit 636 provides control voltages, at node/bus 270 to second input circuit 215B for controlling its impedance to reduce the common mode noise signal at the ECG signal output node 235.

Example Feedback Controller Circuit

Figure 6B:
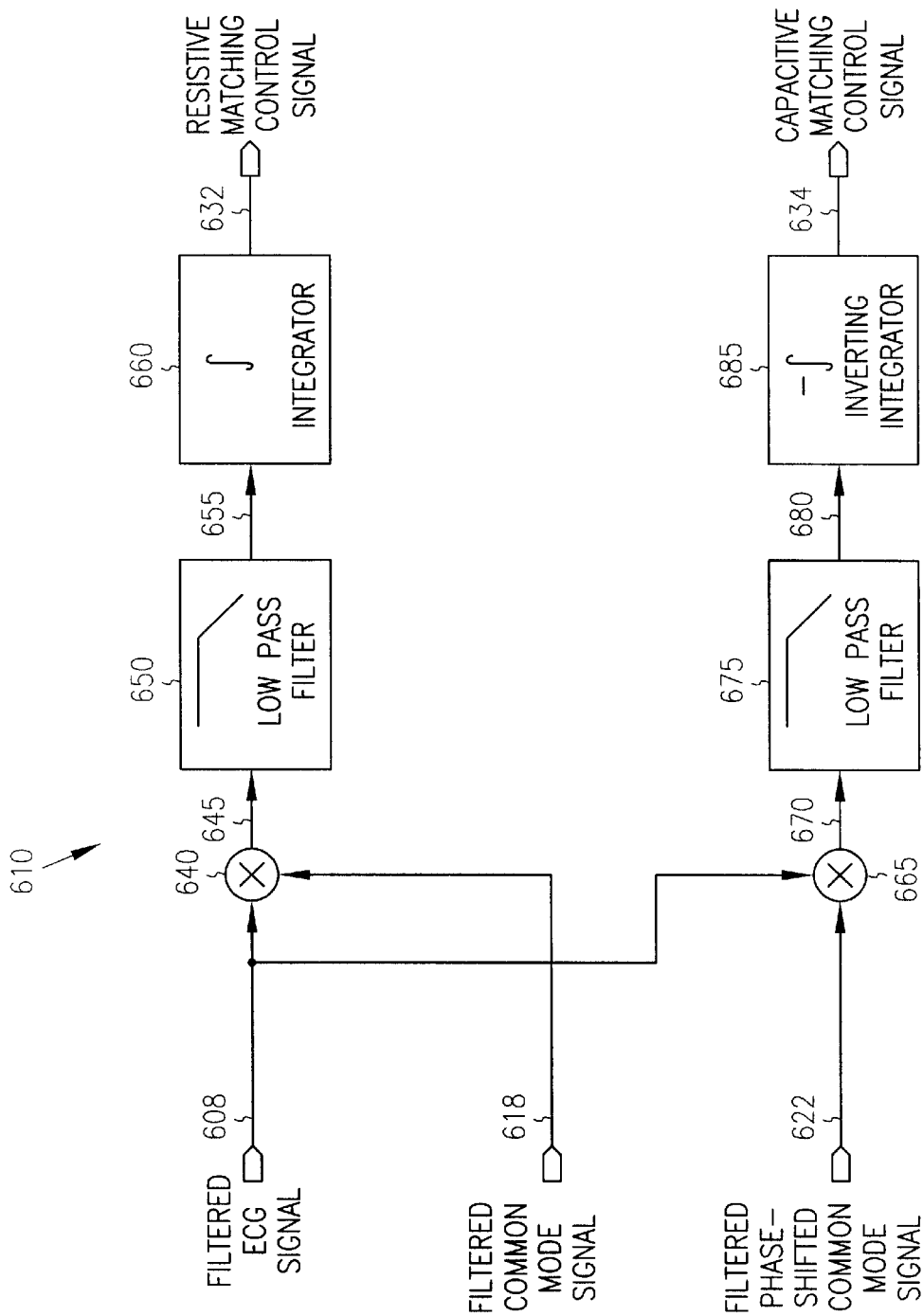
FIG. 6B is a schematic/block diagram illustrating generally one embodiment of a feedback controller circuit portion of the impedance circuit.

FIG. 6B is a schematic/block diagram illustrating generally, by way of example, but not by way of limitation, one embodiment of feedback controller circuit 610. Feedback controller circuit 610 receives the filtered ECG signal, at node 608, the filtered common mode signal, at node 618, and the filtered phase-shifted common mode signal at node 622.

In one embodiment, the filtered common mode signal, at node 618, is phase-detected with respect to the filtered ECG output signal, at node 608, as described below. The filtered ECG signal at node 608 is mixed or multiplied with the filtered common mode signal, at node 618, by a mixer or multiplier (referred to interchangeably herein) such as analog multiplier 640, which provides a resulting signal, referred to as an in-phase signal, at node 645. The in-phase signal at node 645 is received by low pass filter 650. In one embodiment, low pass filter 650 attenuates frequency components above a cutoff frequency of approximately 40 Hertz, and provides a resulting low pass filtered in-phase signal, at node 655, to integrator 660. Integrator 660 integrates the low pass filtered in-phase signal, providing a resulting resistive-matching control signal, at node 632, to impedance control subcircuit 636.

The filtered phase-shifted common mode signal, at node 622, is phase-detected with respect to the filtered ECG output signal, at node 608, as described below. The filtered ECG signal at node 608 is mixed or multiplied with the filtered phase-shifted common mode signal, at node 622, by a mixer or multiplier, such as analog multiplier 665, which provides a resulting signal, referred to as a quadrature phase signal, at node 670. The quadrature phase signal at node 670 is received by low pass filter 675. In one embodiment, low pass filter 675 attenuates frequency components above a cutoff frequency of approximately 40 Hertz, and provides the resulting low pass filtered quadrature phase signal, at node 680, to an integrator, such as inverting integrator 685. Inverting integrator 685 integrates and inverts the low pass filtered quadrature phase signal, providing a resulting capacitive-matching control signal, at node 634, to impedance control subcircuit 636.

Example Impedance Control Subcirciut

FIG. 7 is a schematic diagram illustrating generally, by way of example, but not by way of limitation, one embodiment of portions of impedance control subcircuit 636. In this embodiment, impedance control subcircuit 636 includes one or more variable gain or similar circuits, such as analog multiplier circuits, or first voltage controlled amplifier (VCA) 700A and second VCA 700B. A negative input of each of VCAs 700A–B is grounded. A positive input of each of VCAs 700A–B is coupled to node 220B to receive the output signal from second input circuit 215B.

In one embodiment, the gain of first VCA 700A is adjusted by the resistive-matching control signal received at node 632 from feedback controller circuit 610. The gain of second VCA 700B is adjusted by the capacitive-matching control signal received at node 634 from feedback controller circuit 610. The gain of respective VCAs 700A–B is increased for more positive signals at respective nodes 632 and 634, and decreased for more negative signals at respective nodes 632 and 634. First VCA 700A provides an output voltage, at node 270A, to resistor 360B in second input circuit 215B. Second VCA 700B provides an output voltage, at node 270B, to capacitor 375B in second input circuit 215B.

FIG. 4 illustrates resistor 360B and capacitor 375B as being part of second input circuit 215B, for convenience of illustrating similarities and differences between first and second input circuits 215A–B. It is understood, however, that resistor 360B and capacitor 375B are alternatively regarded as being part of impedance control subcircuit 636 rather than as being part of second input circuit 215B (or other portion of impedance circuit 239) and could alternatively be illustrated therewith.

In one embodiment, first and second VCAs 700A–B provide independent impedance bootstraps, as discussed above with respect to amplifier 350A in first input circuit 215A. However, the gain of first and second VCAs 700A–B is adjusted by feedback controller circuit 610 to control the respective node voltages 270A–B to substantially offset or approximately correct the impedance mismatch between electrodes 110A–B. As a result, the effective signal attenuation from the input of electrode 110A to node 220A is approximately equal to the effective signal attenuation from the input of electrode 110B to node 210B. This, in turn, decreases the common-mode noise at ECG signal output node 235, such that the ECG signal is more readily discernable at node 235.

Example Operation of Impedance Circuit

Figure 8A:
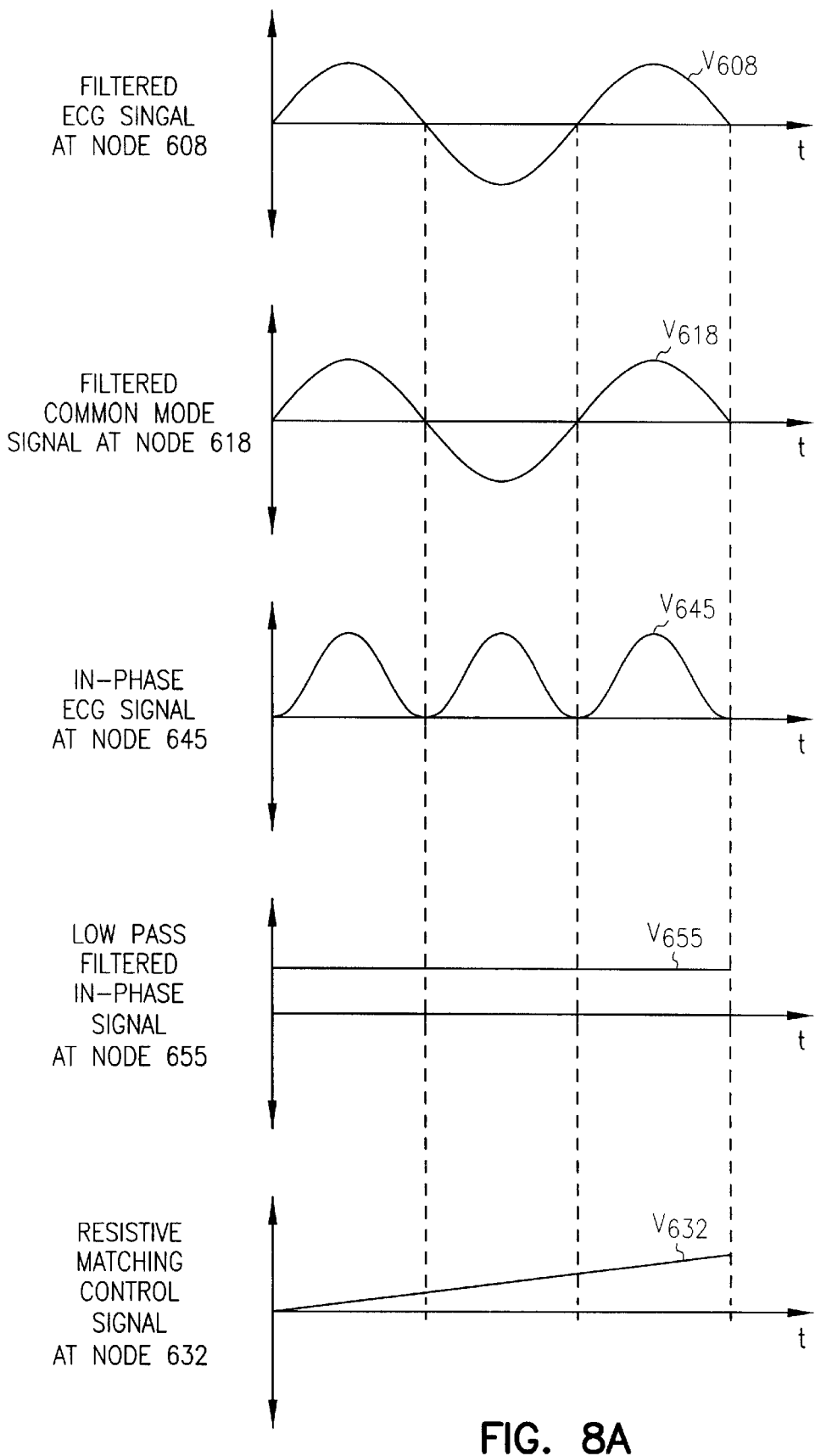
FIG. 8A is a signal waveform diagram illustrating generally one embodiment of operating a feedback controller circuit in which a filtered ECG signal is substantially in phase with a filtered common mode signal.

FIG. 8A is a signal waveform diagram illustrating generally, by way of example, but not by way of limitation, one embodiment of operating impedance circuit 239. In FIG. 8A, $V_{608}$ represents an illustrative example of a filtered ECG signal at node 608 and $V_{618}$ represents an illustrative example of a filtered common mode signal at node 618. In the example illustrated in FIG. 8A, $V_{608}$ and $V_{618}$ are in phase with each other. The signals $V_{608}$ and $V_{618}$ are multiplied with each other at multiplier 640, providing $V_{645}$, a resulting in-phase signal at node 645. For the illustrated signals $V_{608}$ and $V_{618}$, which are in phase with each other, the resulting in-phase signal at node 645 is frequency-doubled and positive-valued. The in-phase signal at node 645 is filtered by low pass filter 650, which attenuates high-frequency components, resulting in a positive-valued signal $V_{655}$ at node 655. The low pass filtered in-phase signal at node 655 is integrated by integrator 660, resulting in an upward ramping resistive-matching control signal, $V_{632}$ at node 632. An increase in the resistive-matching control signal at node 632 increases the gain of first VCA 700A, which increases the effective resistance of resistor 360B.

Figure 8B:
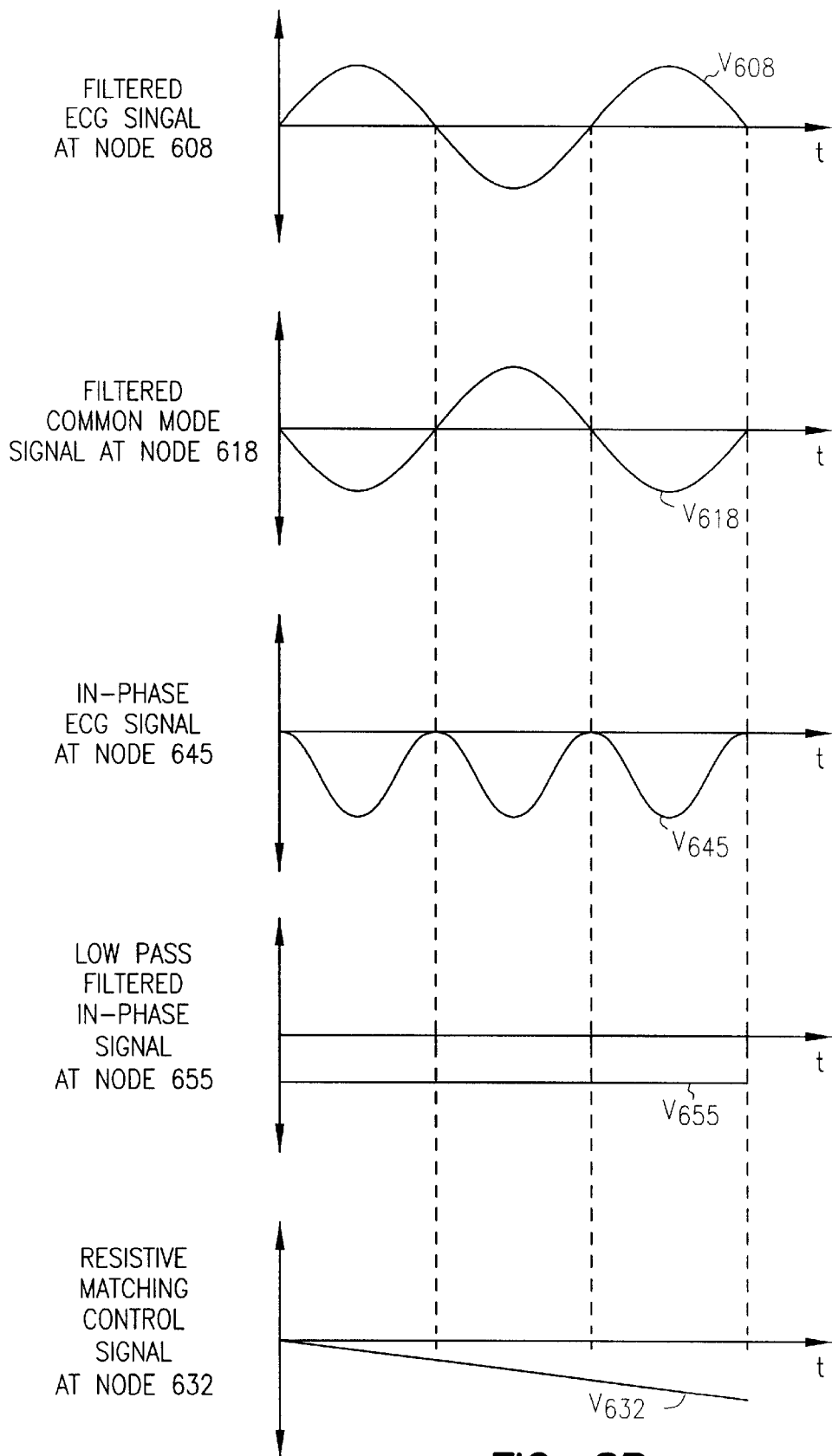
FIG. 8B is a signal waveform diagram illustrating generally one embodiment of operating a feedback controller circuit in which a filtered ECG signal is substantially 180 degrees out of phase with a filtered common mode signal.

FIG. 8B is a signal waveform diagram, similar to FIG. 8A, but providing an illustrative example of signals $V_{608}$ and $V_{618}$ being out of phase with each other. After multiplication, the resulting in-phase signal $V_{645}$ at node 645 is frequency doubled and negative-valued. As a result, the low pass filtered in-phase signal $V_{655}$ at node 655 is also negative-valued. Integration yields a downward ramping resistive-matching control signal $V_{632}$ at node 632, which decreases the gain of first VCA 700A, and decreases the effective resistance of resistor 360B.

Figure 9A:
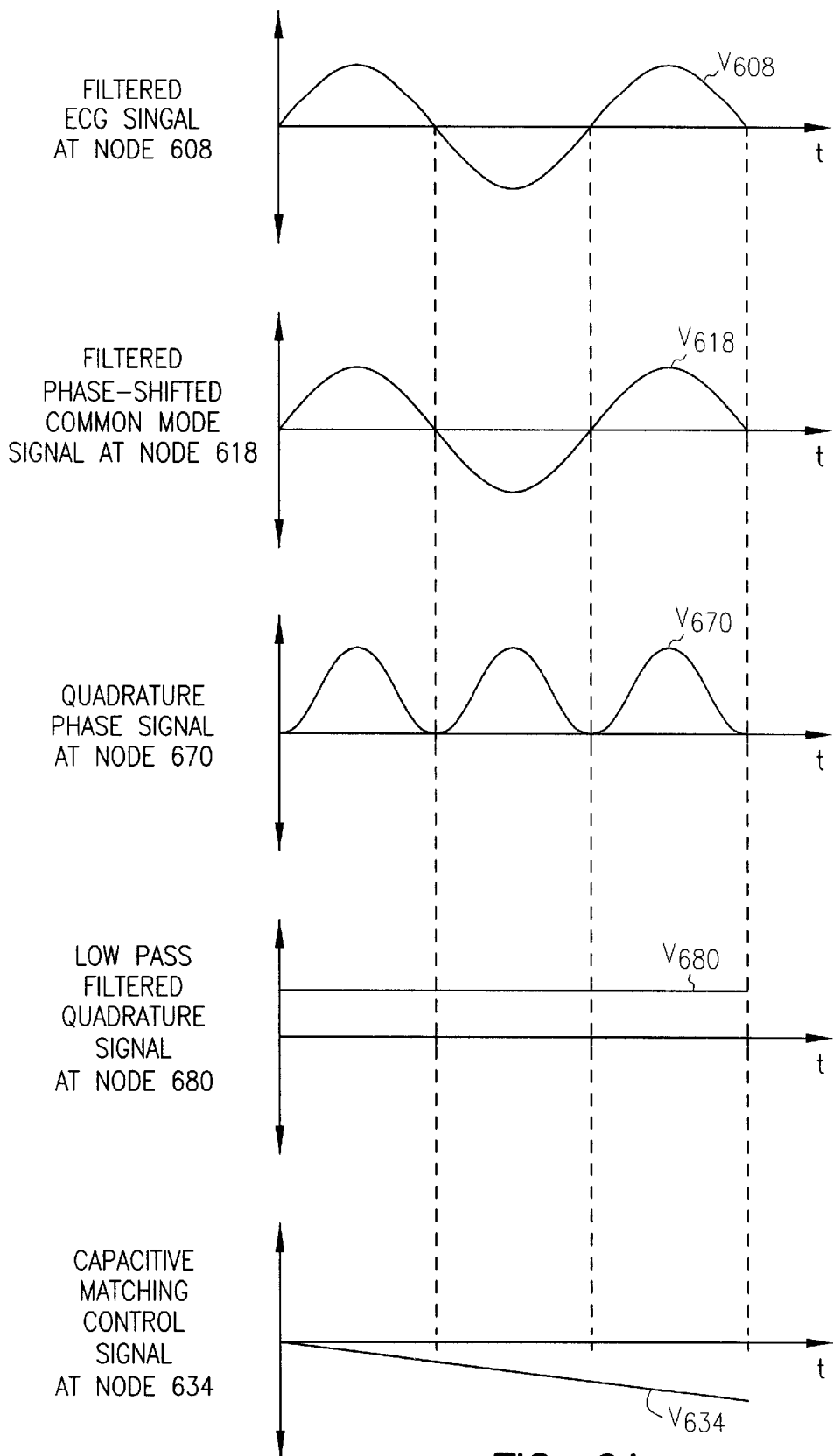
FIG. 9A is a signal waveform diagram illustrating generally one embodiment of operating a feedback controller circuit in which a filtered ECG signal is substantially in phase with a filtered phase-shifted common mode signal.

FIG. 9A is a signal waveform diagram illustrating generally, by way of example, but not by way of limitation, another aspect of one embodiment of operating impedance circuit 239. In FIG. 9A, $V_{608}$ represents an illustrative example of a filtered ECG signal at node 608 and $V_{618}$ represents an illustrative example of a filtered phase-shifted common mode signal at node 618. In the example illustrated in FIG. 9A, $V_{608}$ and $V_{618}$ are in phase with each other. The signals $V_{608}$ and $V_{618}$ are multiplied with each other at multiplier 665, providing $V_{670}$, resulting quadrature-phase signal at node 670. For the illustrated signals $V_{608}$ and $V_{618}$, which are in phase with each other, the resulting quadrature-phase signal at node 670 is frequency-doubled and positive-valued. The quadrature-phase signal at node 670 is filtered by low pass filter 675, which attenuates high-frequency components, resulting in a positive-valued signal $V_{680}$ at node 680. The low pass filtered quadrature-phase signal at node 680 is integrated and inverted by inverting integrator 685, resulting in a downward ramping capacitive matching control signal at node 634. A decrease in the capacitive matching control signal at node 634 decreases the gain of second VCA 700B, which increases the effective capacitance of capacitor 375B.

Figure 9B:
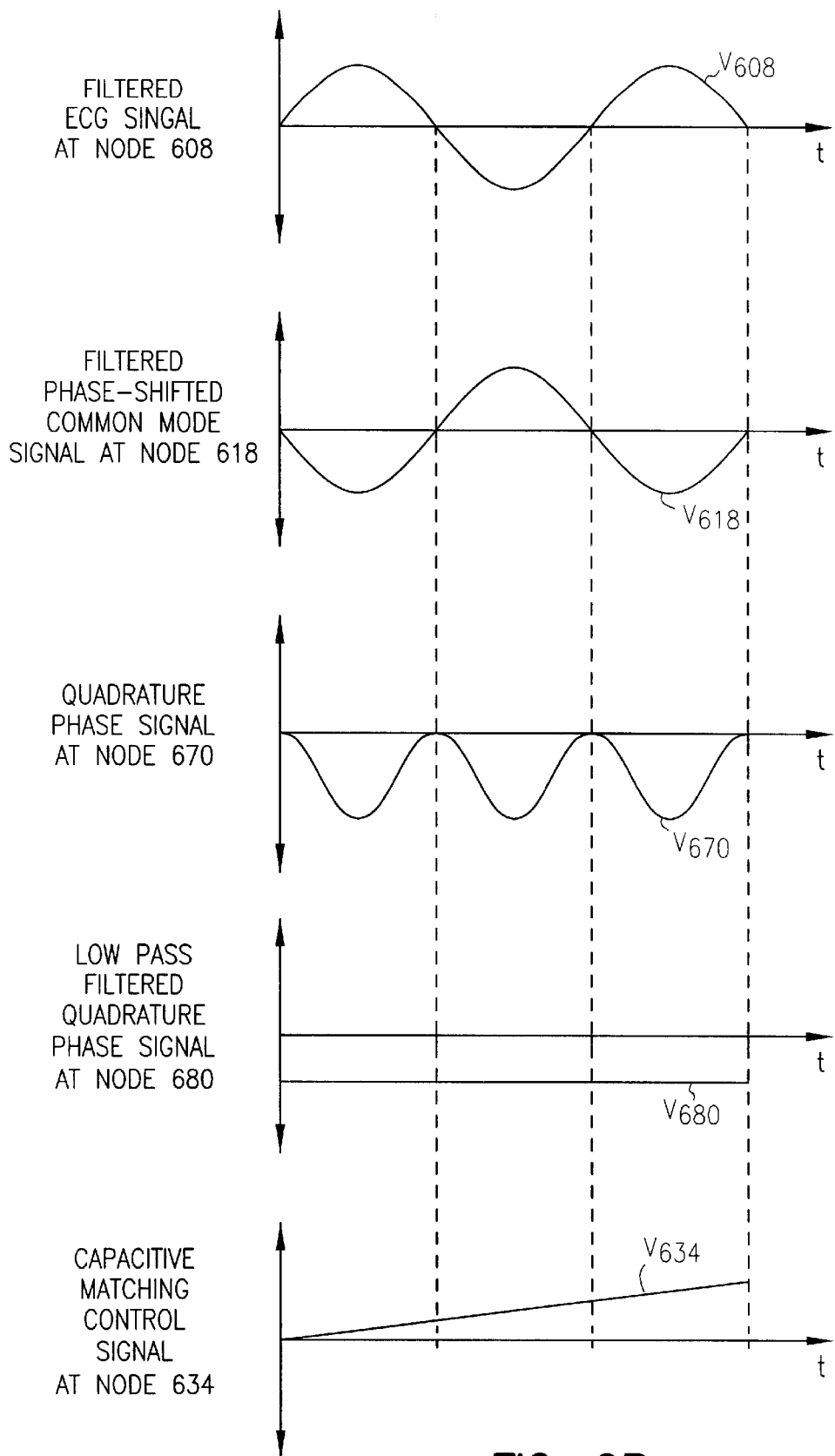
FIG. 9B is a signal waveform diagram illustrating generally one embodiment of operating a feedback controller circuit in which a filtered ECG signal is substantially 180 degrees out of phase with a filtered phase-shifted common mode signal.

FIG. 9B is a signal waveform diagram, similar to FIG. 9A, but providing an illustrative example of signals $V_{608}$ and $V_{618}$ being out of phase with each other. After multiplication, the resulting quadrature-phase signal at node 670 is frequency-doubled and negative-valued. As a result, the low pass filtered quadrature-phase signal at node 680 is also negative-valued. Integration and signal inversion by inverting integrator 685 yields an upward ramping capacitive matching control signal at node 634, which increases the gain of second VCA 700B, and decreases the effective capacitance of capacitor 375B.

FIGS. 8A–B provide illustrative examples of the phase relationship between the filtered ECG signal at node 608 and the filtered common mode signal at node 618. According to one aspect of operation, impedance circuit 239 provides a negative feedback configuration that tends to minimize the magnitude of the low pass filtered in-phase signal at node 655. This effectively matches the effective resistance of resistor 360B in second input circuit 215B to the effective resistance seen at node 345A in first input circuit 215A (when the resistor 200A of first electrode 110A is approximately equal to the resistor 200B of second electrode 110B and the capacitor 205A of first electrode 110A is approximately equal to the capacitor 205B of second electrode 110B).

Similarly, FIGS. 9A–B provide illustrative examples of the phase relationship between the filtered ECG signal at node 608 and the filtered phase-shifted common mode signal at node 618. Impedance circuit 239 provides a negative feedback configuration that tends to minimize the magnitude of the low pass filtered quadrature phase signal at node 680. This effectively matches the effective capacitance of capacitor 375B in second input circuit 215B to the effective capacitance seen at node 345A in first input circuit 215A (when the resistor 200A of first electrode 110A is approximately equal to the resistor 200B of second electrode 110B and the capacitor 205A of first electrode 110A is approximately equal to the capacitor 205B of second electrode 110B).

Even when the resistor 200A of first electrode 110A is not approximately equal to the resistor 200B of second electrode 110B and the capacitor 205A of first electrode 110A is not approximately equal to the capacitor 205B of second electrode 110B, the gain/attenuation from the input of electrode 110A to node 345A in first input circuit 215A is kept substantially identical to the gain/attenuation from the input of electrode 110B to node 345B in second input circuit 215B. As a result, the gain/attenuation from the input of electrode 110A to node 220A is approximately equal to the gain/attenuation from the input of electrode 110B to node 220B. This, in turn, keeps the common mode noise signal at node 245 at a reasonably small value, improving the signal-to-noise characteristics of the ECG signal at node 235.

Example Test Results

Operation of one embodiment of a voltage sensing circuit was simulated using a SPICE computer simulation. The component values that were used are listed below (by way of example, but not by way of limitation).

First electrode 110A: $R_{200A}$=26 KΩ, $C_{205A}$=25 nF. First input circuit 215A: $R_{300A}$=10 KΩ, $R_{335A}$=10 KΩ, $C_{340A}$=240 nF, $R_{360A}$=10 MΩ, $C_{375A}$=120 pF, $R_{370}$=2.6 KΩ, $R_{355}$=1 KΩ. Second electrode 110B: $R_{200B}$=20 KΩ, $C_{205B}$=10 nF. Second input circuit 215B: $R_{300B}$=10 KΩ, $R_{335B}$=10 KΩ, $C_{340B}$=240 nF, $R_{360B}$=12 MΩ, $C_{375B}$=300 pF. Averager 230: $R_{510}$=100 KΩ, $R_{512}$=50 KΩ, $R_{515}$=50 KΩ. Phase Shifter 620: $C_{535}$=6 nF, $R_{530}$=100 KΩ (configured as a differentiator). Filters 606 and 616 were configured as high pass filters and each included an RC network where R=10 MΩ and C=10 nF. Low pass filters 650 and 675 each included an RC network where R=400 KΩ and C=10 nF. Integrators 660 and 685 each included an RC integration time constant where R=800 KΩ and C=100 nF.

Figure 10:
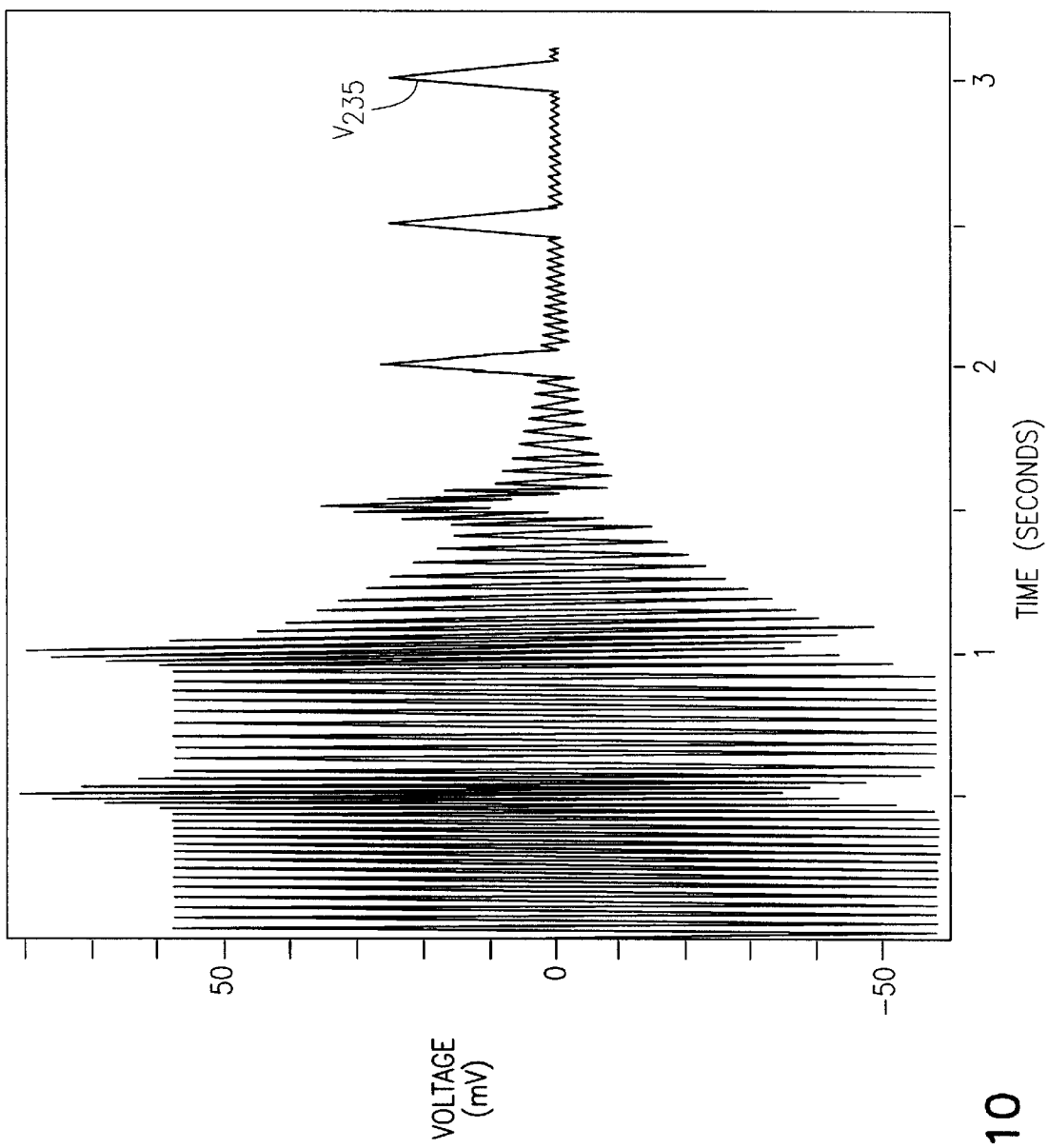
FIG. 10 is a computer simulation signal waveform diagram showing an ECG output signal (where electrode impedances are mismatched) before and after activation of the impedance circuit.

FIG. 10 is a computer simulation signal waveform diagram, using above-described component values having mismatched electrode impedances, and showing the ECG output signal at node 235. Before time t=1 second, the feedback controller circuit was turned off, and the ECG output signal is swamped by common mode-noise. At time t=1 second, the impedance circuit 239 was activated. As illustrated in FIG. 10, this initiated the gain/attenuation matching described above. As a result, the common mode noise signal was substantially reduced, as illustrated in FIG. 10 for times greater than 2 seconds, such that the underlying ECG signal waveform was readily discernable as having good signal-to-noise characteristics. The circuit was also resimulated with the impedance mismatch being incorporated into the opposite electrodes, and obtained similar results.

Alternate Embodiment #2

Figure 11:
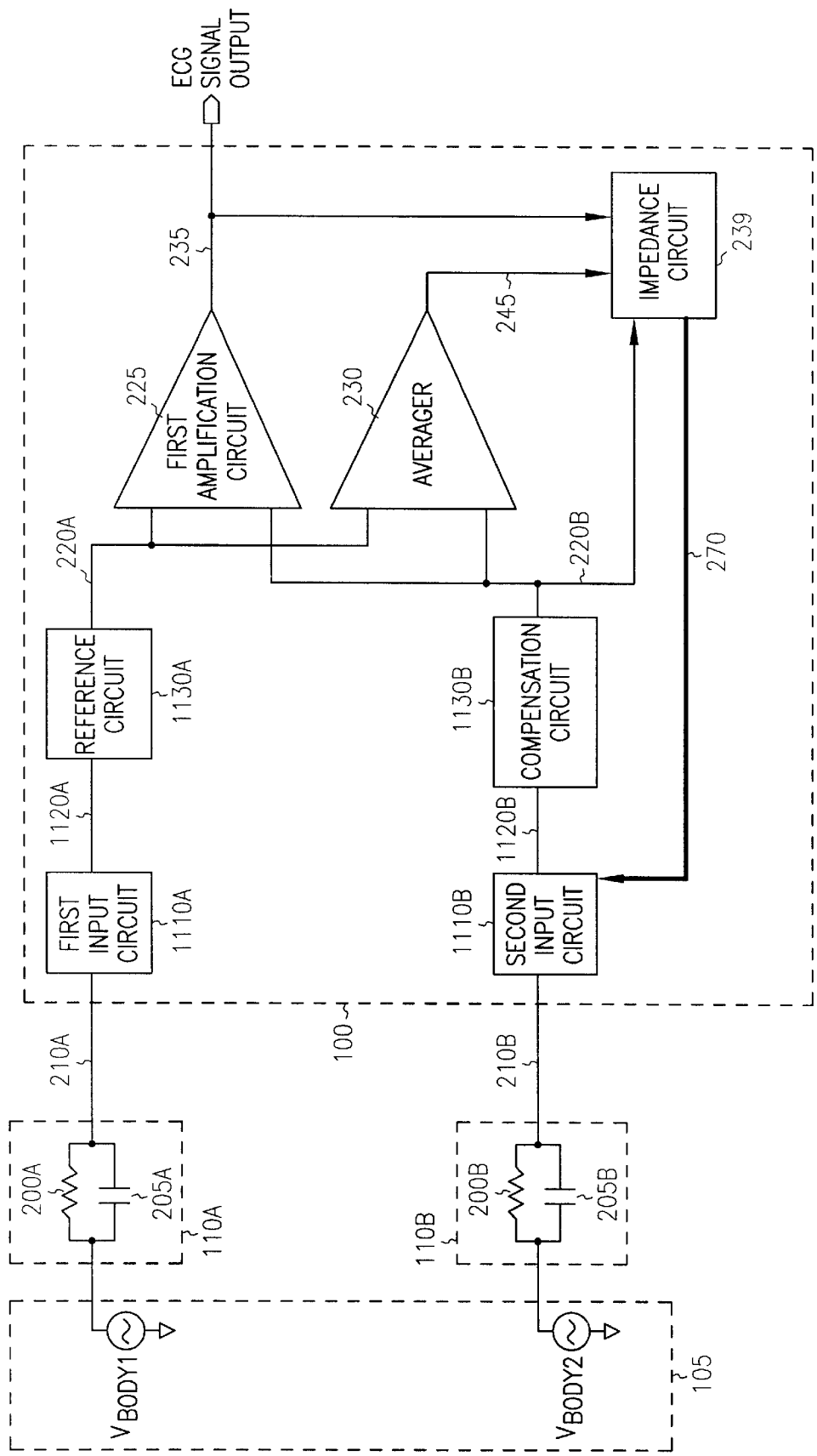
FIG. 11 is a schematic/block diagram that illustrates generally another embodiment of portions of a voltage sensing system, such as an ECG detector.

FIG. 11 is a schematic/block diagram, similar to FIG. 2, that illustrates generally, by way of example, but not by way of limitation, another embodiment of portions of a voltage sensing system, such as ECG detector 100, and an environment in which it is used. In addition to what is shown in FIG. 2, FIG. 11 includes a reference circuit 1130A and a compensation circuit 1130B. The reference circuit 1130A is coupled at node 1120A, to receive the output of the first input circuit 1110A. The output of the reference circuit 1130A is coupled to node 220A. Similarly, the compensation circuit 1130B is coupled at node 1120B, to receive the output of the second input circuit 1110B. The output of the compensation circuit 1130B is coupled to node 220B. Nodes 220A–B is coupled to both of first amplification circuit 225 and averager 230 circuitry.

As discussed above, the effective impedances of first electrode 110A and second electrode 110B may be different. This causes the amount of signal attenuation from the input of electrode 110A to node 210A to be different from the amount of signal attenuation from the input of electrode 110B to node 210B. According to prior art techniques, this resulted in unwanted common-mode noise signal amplitude, at node 235, that exceeds the desired ECG signal amplitude at node 235. According to one aspect of the present system, before feeding the outputs of the first and second input circuits to the impedance circuit 239, to compensate for impedance mismatches between electrodes 110A–B, the output of the electrodes are fed to first and second input circuits 110A–B including buffer amplifiers to circumvent the problems associated with high capacitance cables, instead of compensating skin-electrode impedance mismatches at the input, a separate reference circuit 1130A and a compensation circuit 1130B follows the input circuitry 1110A–B. This allows a constant high impedance at the input, and reduces the cable loading effects on the impedance balancing. Later the output of the reference and compensation circuits 1130A–B are fed to the impedance circuit 239 to substantially offset, correct, or compensate for effects of the impedance mismatch between electrodes 110A–B. As a result, the effective signal attenuation from the input of electrode 110A to node 220A is approximately equal to the effective signal attenuation from the input of electrode 110B to node 210B. This, in turn, decreases the common-mode noise and high capacitance problems at ECG signal output node 235, such that the desired ECG signal is more readily discernable at node 235. Additionally this reduces the cable loading effects on the impedance balancing.

Examples of Input Circuits Including Buffer Amplifiers

FIG. 12A is a schematic diagram, similar to FIG. 3A, illustrating generally, by way of example, but not by way of limitation, one embodiment of first input circuit 1110A. In place of the amplifier 350A of input circuit 215A shown in FIG. 3A, the input circuit 1110A shown in FIG. 12A includes a buffer amplifier 1350A having an output at node 1120A. Also the input circuit 1110A does not have the phase shifter 330A, and the feedback resistor 355 of input circuit 215A shown in FIG. 3A. Phase shifting is accomplished at a later stage in the reference circuit 1130A.

FIG. 12B is a schematic diagram, similar to FIG. 3B, illustrating generally, by way of example, but not by way of limitation, one embodiment of second input circuit 1110B. Operation of correspondingly numbered elements (but with a different suffix letter "B") is as described with respect to FIG. 12A. The second input circuit does not have the phase shifter 330B shown in FIG. 3B. Phase shifter is included later in the compensation circuit 1130B. In FIG. 12B, however, the second input circuit 1110B does not receive the signals from the impedance circuit 239 as shown in second input circuit 215B to adjust the output voltage of the second input circuit 215B. In this embodiment, the adjustments to the output voltages by the impedance circuit are done at a later stage by a compensation circuit 1130B to compensate for skin-electrode impedance mismatches at the input electrodes 110A–B.

Example of Reference Circuit

Figure 13A:
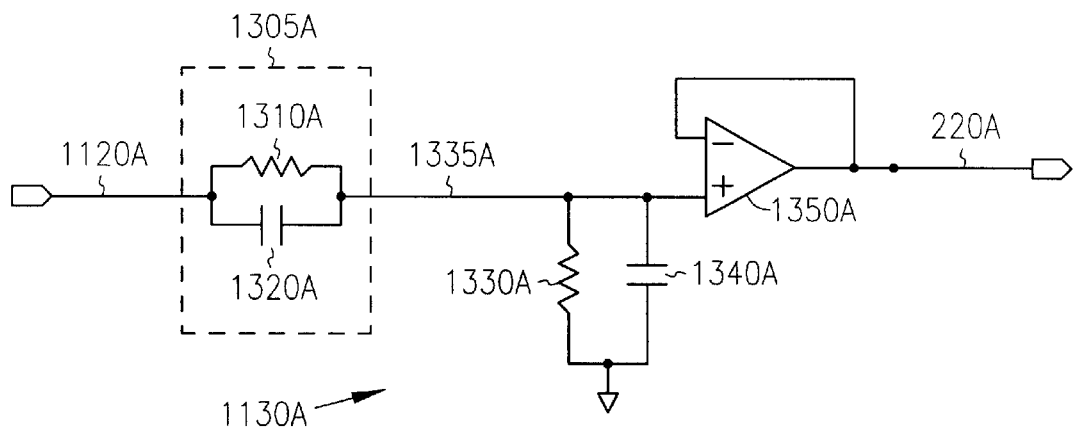
FIG. 13A is a schematic diagram illustrating generally one embodiment of a reference circuit.

FIG. 13A is a schematic diagram illustrating generally, by way of example, but not by way of limitation, one embodiment of reference circuit 1130A. The reference circuit 1130A receives input signal at node 1120A from first input circuit 1110A. In one embodiment, the reference circuit also includes a phase shifter 1305A. In one example, phase shifter 1305A includes a series phase lead network formed by resistor 1310A in parallel with capacitor 1320A. An output of the phase shifter 1305A is coupled at node 1335A, to a positive input of amplifier 1350A. An output, at node 220A, of amplifier 1350A is fed back to its negative input. Input capacitor 1340A is coupled between the positive input, at node 1335A, of amplifier 1350A, and the ground node.

Example of Compensation Circuit

Figure 13B:
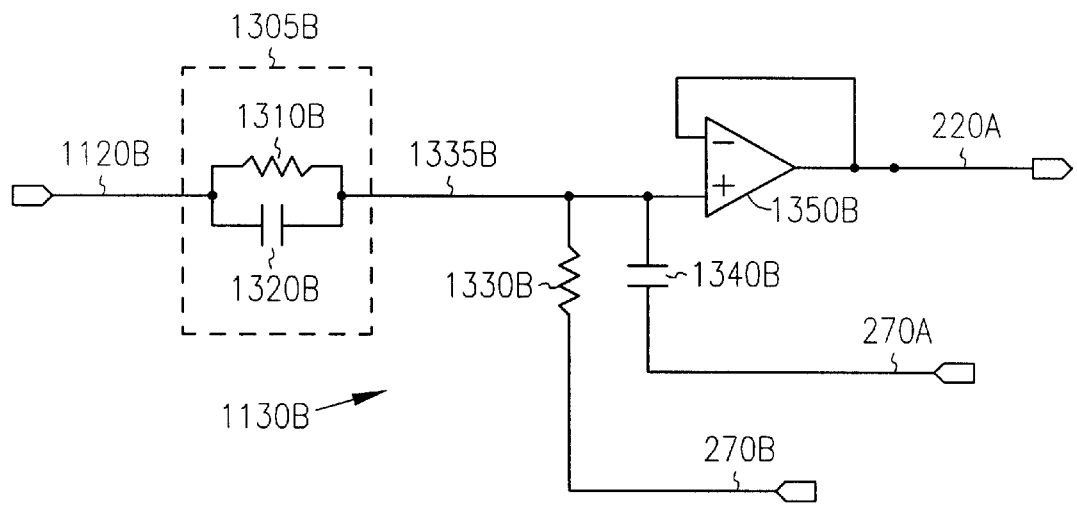
FIG. 13B is a schematic diagram illustrating generally one embodiment of a compensation circuit.

FIG. 13B is a schematic diagram illustrating generally, by way of example, but not by way of limitation, one embodiment of compensation circuit 1130B. The compensation circuit 1130B receives input signal at node 1120B from second input circuit 1110B. As described in FIG. 13A, the compensation circuit 1130B shown in FIG. 13B is similar to reference circuit 1130A. Operation of corresponding umbered elements (but with a different suffix letter "B") is as described with respect to FIG. 3A. In FIG. 13B, however, input resistor 1330B couples a signal received at node 270A, from impedance circuit 239, to the positive input, at node 1335B, of amplifier 1350B. Similarly, input capacitor 1340B couples a signal received at node 270B, from impedance circuit 239, to the positive input, at node 1335B, of the amplifier 1350B. As described in FIG. 4A, the adjustment of the voltages at nodes 270A–B are similar to second input circuit 215B.

Example Impedance Control Subcircuit

Figure 14:
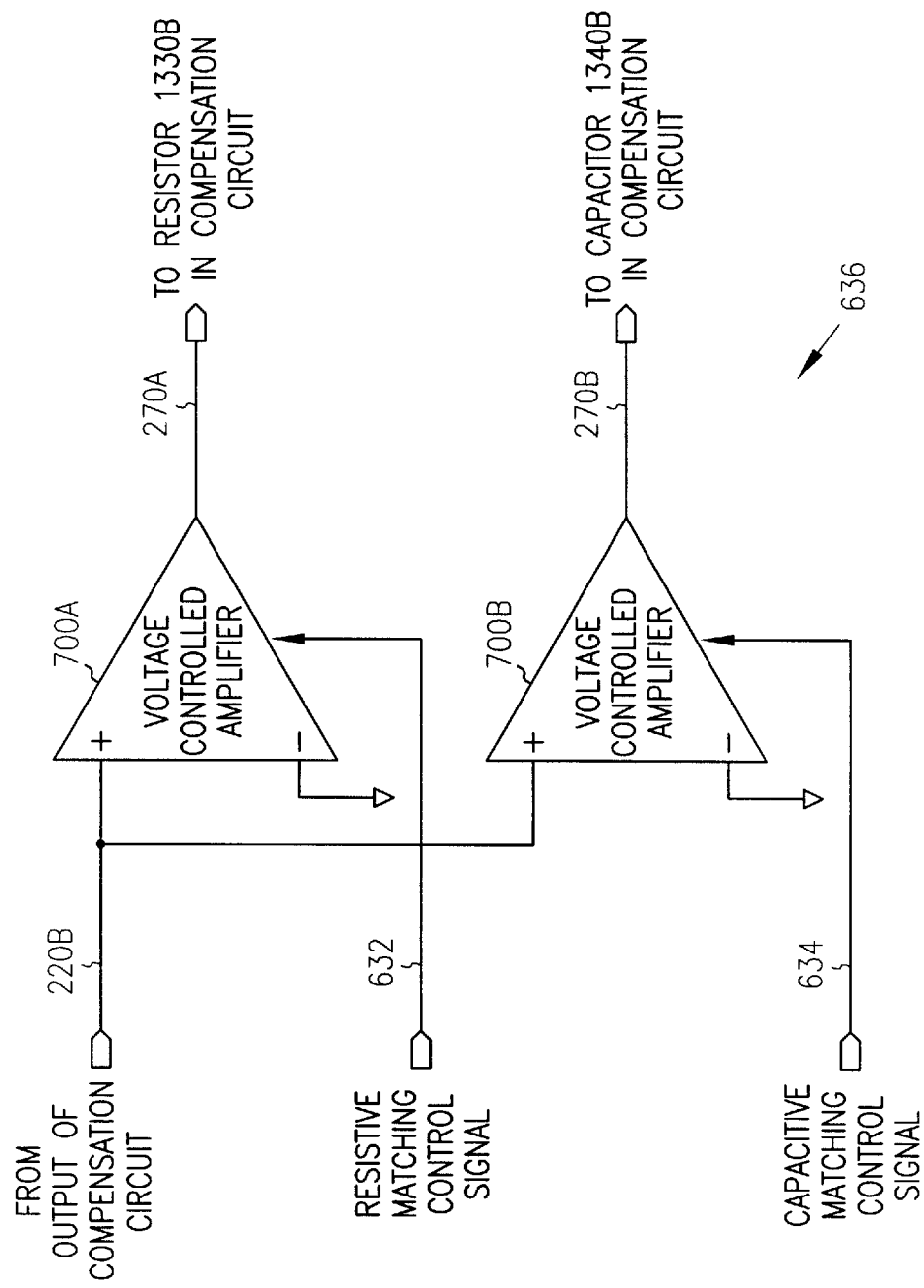
FIG. 14 is a schematic diagram illustrating generally another embodiment of an impedance control sub-circuit.

FIG. 14 is a schematic diagram, similar to FIG. 7, illustrating generally, by way of example, but not by way of limitation, one embodiment of portions of impedance control sub-circuit 636. In FIG. 14, however the positive input of each of VCAs 700A–B is coupled to node 220B to receive the output signal from compensation circuit 1130B. Also the outputs of VCAs 700A–B, at nodes 270A–B, are provided to resistor 1330B and capacitor 1340B respectively.

Example Test Results

Operation of one embodiment of a voltage sensing circuit was constructed using following components (component values that were used are listed below by way of example, but not by way of limitation).

First input circuit 1110A: $R_{300A}$=10 KΩ, $C_{375A}$=1.5 nF, and $R_{360A}$=10 MΩ. Second input circuit 1110B: $R_{300B}$=10 KΩ, $C_{375}$=1.5 nF, and $R_{360}$=10 MΩ. Reference input circuit 1130A: $R_{1310A}$=43 KΩ, $C_{1320A}$=47 nF, $R_{1330A}$=3 MΩ, and $C_{1340A}$=1.5 nF. Compensation Circuit 1130B: $R_{1310B}$=43 KΩ, $C_{1320B}$=47 nF, $R_{1330B}$=1 MΩ, and $C_{1340B}$=3.3 nF.

Figure 15A:
FIG. 15A is a timing diagram illustrating how the voltage sensing system quickly corrects for the unwanted common-mode noise signal resulting from a change in impedance between the first and second electrodes.
Figure 15B:
FIG. 15B is another timing diagram illustrating how the voltage sensing system quickly corrects for the unwanted common-mode noise signal resulting from a change in impedance between the first and second electrodes.

FIG. 15A is a timing diagram illustrating generally, by way of example, but not by way of limitation, one embodiment of an ECG signal showing the effect of change (transient changes) in series impedance between first and second electrodes 110A and 110B, when the effective impedance at first and second electrodes 110A–B are changed by inserting a 51 KΩ resistor and 47 nF capacitor in series between the second electrode 110B and the voltage sensing system 100 (transient changes shown starting at point 1510 and subsiding at point 1520). Further, FIG. 15A illustrates generally, by way of example, how the voltage sensing system 100 quickly corrects for the resulting unwanted common-mode noise signal due to the change in impedance in the lead connecting the second electrode 110B. FIG. 15B is another timing diagram, similar to FIG. 15A, illustrating generally, by way of example, but not by way of limitation, how the voltage sensing system 100 corrects for resulting unwanted common-mode noise signal amplitude when the 51 KΩ resistor and the 47 nF capacitor are removed (transient changes shown starting at point 1530 and subsiding at point 1540), resulting in the change in impedance between the leads connecting the electrodes 110A and 110B (impedance's of the two leads become equal).

Figure 15C:
FIG. 15C is another timing diagram illustrating how the voltage sensing system quickly corrects for the unwanted common-mode noise signal resulting from a change in impedance between the first and second electrodes.

FIGS. 15C is another timing diagram, similar to FIG. 15A, illustrating generally, by way of example, but not by way of limitation, how the voltage sensing system 100 corrects for the resulting unwanted common mode noise signal when the effective impedance between electrodes 110A and 110B are changed by inserting a 8.36 KΩ resistor and a 47 nF capacitor in series between the first electrode 110A and the voltage sensing system 100 (transient changes shown starting at point 1550 and subsiding at point 1560).

Figure 15D:
FIG. 15D is another timing diagram illustrating how the voltage sensing system quickly corrects for the unwanted common-mode noise signal resulting from a change in impedance between the first and second electrodes.

FIG. 15D is another timing diagram, similar to FIG. 15B, illustrating again generally, by way of example, but not by way of limitation, how the voltage sensing corrects for resulting unwanted common-mode noise signal when the 8.36 KΩ resistor and the 47 nF capacitor are removed (transient change shown starting at point 1570 and subsiding at point 1580), resulting in the change in impedance between the leads connecting the electrodes 110A and 110B (impedance's of the two leads become equal).

FIGS. 15 A–D, demonstrate that irrespective of the changes in the effective impedance between first and second electrodes 110A–B due to a change in impedance in a lead connecting the first electrode 110A or due to a change in impedance in a lead connecting the second electrode 110B, the voltage sensing system 100 can be effective in correcting for the resulting unwanted common-mode noise signal.

Alternative Embodiment #3

Figure 16:
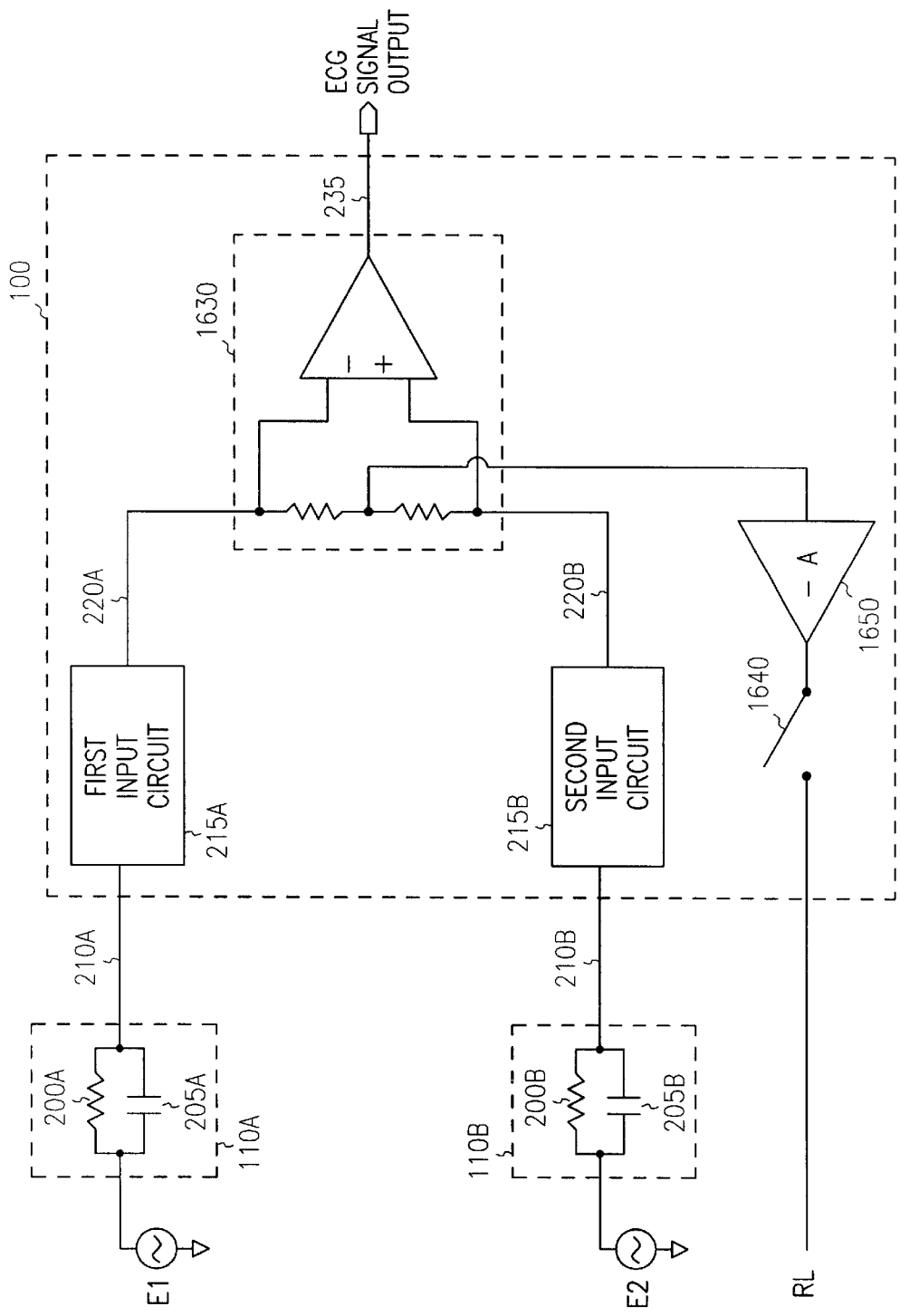
FIG. 16 is a schematic/block diagram that illustrates generally another embodiment of portions of a voltage sensing system, such as an ECG detector including a switch to control flow of right-leg signal into a ECG cable.

FIG. 16 is a schematic/block diagram illustrating generally, by way of example, but not by way of limitation, one embodiment of portions of voltage sensing system, such as an ECG detector 100, having a switch 1640 to disconnect the right-leg drive signal to the ECG cable. The voltage sensing system 100 further includes an inverter 1650. In FIG. 16, body voltages including an electrical heart activity signal are received at first and second electrodes 110A–B, which are modeled schematically. First electrode 110A has an effective skin-electrode impedance modeled by resistor 200A in parallel with capacitor 205A. Similarly, second electrode 110B has an effective skin-electrode impedance modeled by resistor 200B in parallel with capacitor 205B. Electrodes 110A–B are coupled, at respective nodes 210A–B, to respective first and second input circuits 215A–B. Nodes 220A–B is each coupled to differential amplification circuit 1630. In one embodiment, as illustrated in FIG. 16, the differential amplification circuit 1630 includes a differential input, single-ended output amplifier, such as an off-the shelf or other instrumentation amplifier. Amplification circuit receives input signals at nodes 220 A–B from first and second input circuits 215A–B, respectively, and outputs an ECG signal at node 235.

In one embodiment the ECG detector 100, includes a right leg cable RL (used for attaching a third electrode to the right leg of a patient) used in a feedback arrangement coupled to the differential amplification circuit. The third electrode is driven by an offsetting common-mode signal (the common mode signal is inverted and multiplied by an inverter 1650) to reduce the unwanted common-mode noise signal at the ECG inputs. Also shown is the inverter 1650 coupled between the differential amplification circuit 1630, and the switch 1640 attached to the right leg RL cable to disconnect the flow of the right leg RL signal into the ECG cable, when the right leg RL drive electrode is not in use. When the right leg RL drive is not in use, parasitic feedback through the ECG cable capacitance decreases the response range of the impedance balancing circuitry and also slows the transient response. This feature of incorporating the switch 1640 prevents the right leg RL signal from entering the ECG cable, when the right-leg RL electrode is not being used and the impedance balancing is active. This control of the switch 1640 may be implemented in hardware for manual operation or may be implemented by using one or more sequences or steps carried out on a microprocessor or other microcontroller for automatic or display driven operation.

Alternate Embodiment #4

Figure 17:
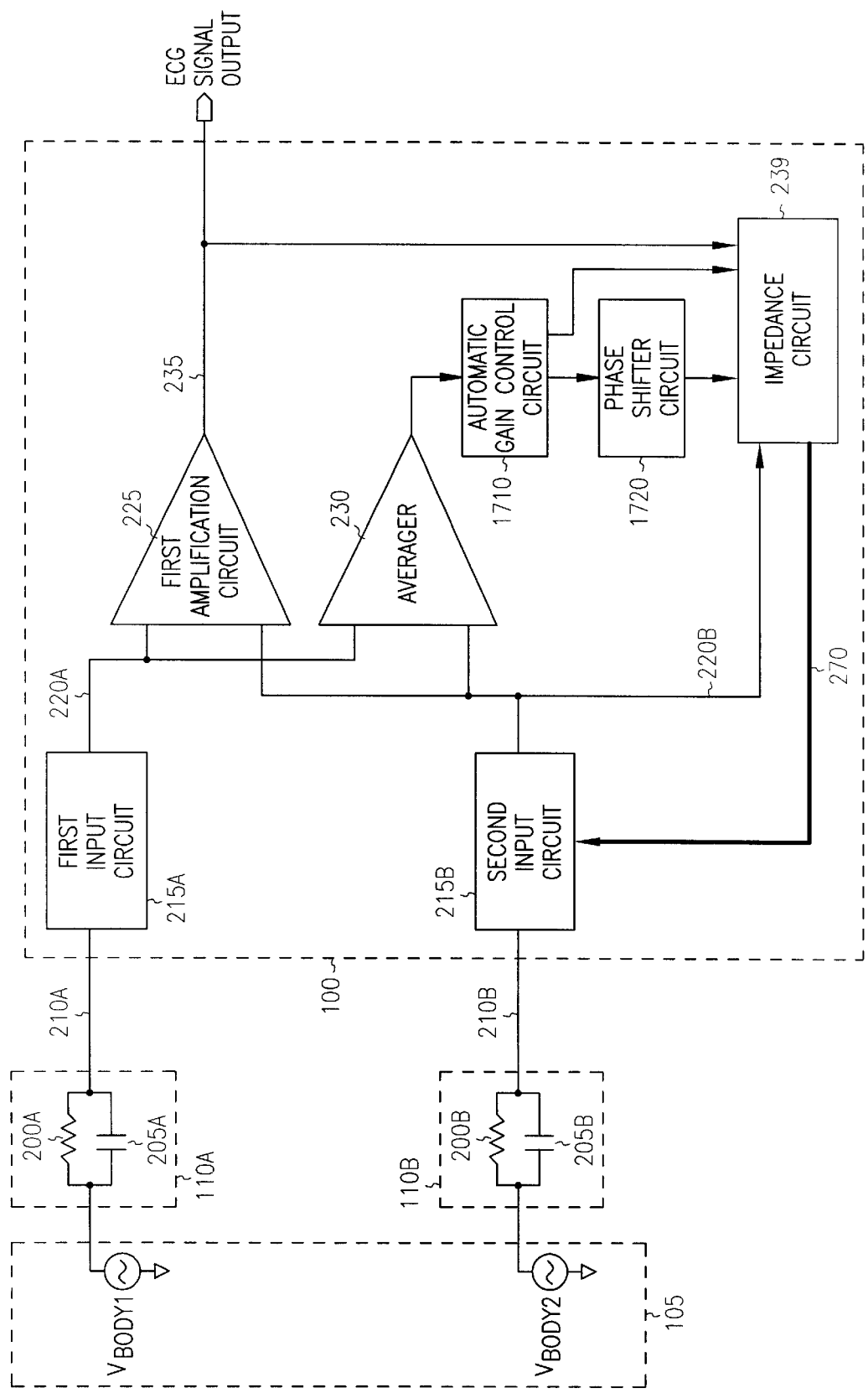
FIG. 17 is a schematic/block diagram that illustrates generally another embodiment of portions of a voltage sensing system, such as an ECG detector including an automatic gain control module.

FIG. 17 is a schematic/block diagram, similar to FIG. 2, that illustrates generally, by way of example, but not by way of limitation, another embodiment of portions of a voltage sensing system, such as an ECG detector 100, and an environment in which it is used. In addition to what is shown in FIG. 2, FIG. 16 includes an automatic gain control circuit 1710 and a phase shifter circuit 1720. The automatic gain control circuit is coupled to receive the common mode signal from the averager 230. The phase shifter circuit 1720 is coupled to receive the output of the automatic gain control circuit 1710. Impedance circuit 239 receives the output of the phase shifter circuit 1720 and the automatic gain control circuit 1710.

The transient response time of the impedance circuit 239 depends on the magnitude of the common-mode input signals. The larger the common-mode signal, the faster the impedance circuit 239 responds. FIG. 16 shows the automatic gain circuit 1710 coupled between the common-mode input signal coming from the averager 230 and the impedance circuit 239 including the filtering 650/675 and multiplier stages 660/685 shown in FIG. 6B. By regulating the amplitude of the common-mode noise, the transient response time can be held essentially constant over a wide range of input noise levels.

Figure 18:
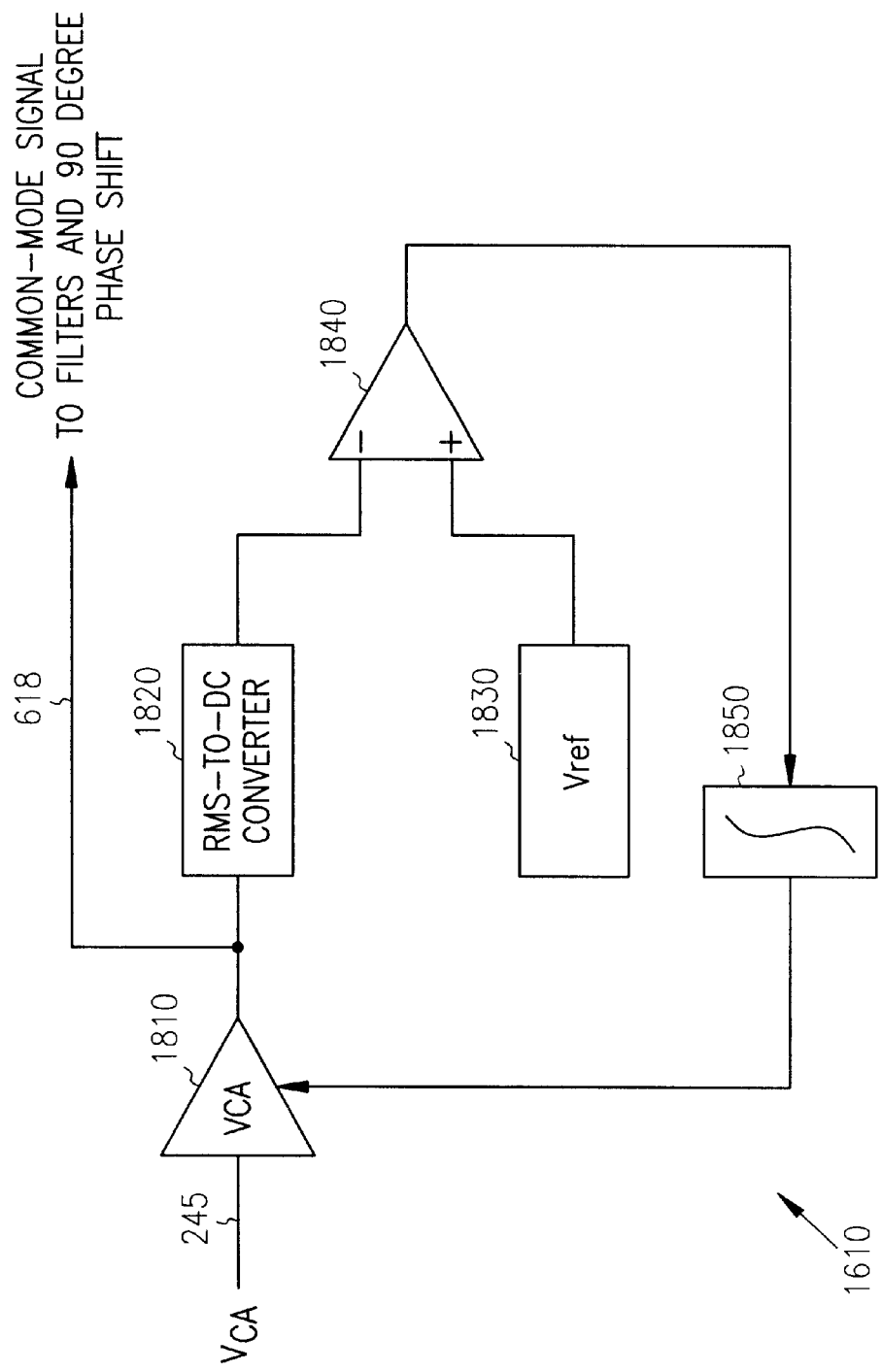
FIG. 18 is a schematic diagram illustrating generally one embodiment of an automatic gain control circuit.

FIG. 18 is a schematic/block diagram illustrating generally, by way of example, but not by way of limitation, one embodiment of automatic gain control circuit 1810. The common-mode input signal from the averager 230 is received at voltage controlled amplifier 1810 through node 245. In one embodiment the automatic gain control circuit 1710 includes a RMS-to-DC converter 1820. The input of the RMS-to-DC 1820 converter is coupled to the output of the voltage-controlled amplifier 1810. The DC signal output of the RMS-to-DC converter is fed to a differential amplifier 1840. Also in this embodiment, the differential amplifier 1840 receives a reference signal from a power source $V_{ref}$ 1830. An integrator 1850 receives the output of the differential amplifier 1840. The voltage-controlled amplifier 1810 receives the output of the integrator. The output of the voltage-controlled amplifier 1810 is also connected to the impedance circuit 239 and phase shifter circuit 1720 via nodes 618. The common-mode signal is boosted by the voltage-controlled amplifier based on the output of the integrator. If the output signal of the integrator is larger, then the gain is decreased, and if the output signal of the integrator is small, then the gain is increased.

Conclusion

The above-described system provides, among other things, a voltage sensing system with input impedance balancing for electrocardiogram (ECG) sensing or other applications. The present system allows sensing of ECG or other input voltage signals and reduces sensing of unwanted common-mode noise signals. The present system does not require the use of more than two electrodes. Instead, a common mode signal is generated from the two electrodes, and a feedback network operates to minimize the common mode signal. It is understood, however, that more than two electrodes can be used in the present system such as, for example, by including a third electrode that provides feedback cancellation of the common mode voltage to further improve its signal-to-noise ratio of the system. It is also understood that signal inversions (such as from inverting integrator 685, for example) can be moved elsewhere in the signal flow.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An apparatus for sensing a difference between first and second input voltages, the apparatus comprising:

a reference circuit, where the reference circuit includes an input receiving an amplified signal based on first input voltage, and an output providing a reference voltage;

a compensation circuit, where the compensation circuit includes an input receiving an amplified signal based on the second input voltage, and an output providing a compensated voltage based on reference voltage;

a first amplification circuit, where the first amplification circuit includes a first input receiving a signal based on the reference voltage, a second input receiving a signal based on the compensated voltage, and an output providing a differential output signal based on a difference between the signals of the first and second inputs of the first amplification circuit;

an averager circuit, where the averager circuit includes a first input receiving a signal based on the reference voltage, a second input receiving a signal based on the compensated voltage, and an output providing a common mode (CM) output signal based on the signals at the first and second inputs of the averager circuit; and an impedance circuit, coupled to receive signals from the outputs of the first amplification and averager circuits, the impedance circuit adjusting an impedance of the compensation circuit, based on the signals received from the outputs of the first amplification circuit and the averager cirucit to reduce an impact of the CM output signal on the ouput of the first amplification circuit.

2. The apparatus of claim 1, further includes a phase-shifter circuit, having an input coupled to the output of the averager circuit, and an output providing a phase-shifted CM output signal.

3. The apparatus of claim 2, in which the phase-shifter circuit includes one of an integrator and a differentiator.

4. The apparatus of claim 2, in which the impedance circuit includes a feedback controller circuit, where the feedback controller circuit includes:

a first mixer, coupled to receive the differential output signal from the first amplification circuit and the CM signal from the averager circuit, and providing a first mixer output based on the differential and CM output signals; and a second mixer, coupled to receive the differential output signal from the first amplification circuit and the phase-shifted CM output signal from the phase-shifter, and providing a second mixer output based on the differential and the phase-shifted CM output signals.

5. The apparatus of claim 4, in which the feedback controller circuit further includes:

a first integrator, having an input coupled to the first mixer output, and providing a first control signal to an impedance control subcircuit; and a second integrator, having an input coupled to the second mixer output, and providing a second control signal to the impedance control subcircuit.

6. The apparatus of claim 5, in which the impedance circuit further includes:

a first filter, coupling the differential output signal from the output of the first amplification circuit to the second mixer;

a second filter, coupling the CM output signal from the output of the phase-shifter circuit to the first mixer; and a third filter, coupling the phase-shifted CM output signal from the output of the phase-shifter circuit to the second mixer.

7. The apparatus of claim 6, in which the feedback controller circuit further includes:

a first low pass filter, coupling the first mixer output to the input of the first integrator; and a second low pass filter, coupling the second mixer output to the input of the second integrator.

8. The apparatus of claim 6, in which the impedance control subcircuit includes:

a first voltage-controlled amplifier (first VCA), having first, second, and gain control inputs, and an output, the first input of the first VCA coupled to receive a signal based on the compensation voltage, the second input of the first VCA coupled to a ground node, the gain-control input of the first VCA coupled to receive the first control signal from the feedback controller, and the output of the first VCA controlling a resistive component of impedance that is coupled to the compensation voltage; and a second VCA, having first, second, and gain-control inputs, and an output, the first input of the second VCA coupled to receive a signal based on the compensation voltage, the second input of the second VCA coupled to the ground node, the gain-control input of the second VCA coupled to receive the second control signal from the feedback controller, and the output of the second VCA controlling a reactive component of the impedance that is coupled to the compensation voltage.

9. The apparatus of claim 8, in which the impedance control subcircuit includes the impedance that is coupled to the compensation circuit, which includes:

a resistor, controlled by the output of the first VCA; and a capacitor, controlled by the output of the second VCA.

10. The apparatus of claim 1, further comprises a first input circuit coupled between a first electrode and the input of the reference circuit.

11. The apparatus of claim 10, in which the first input circuit includes an impedance bootstrap circuit.

12. The apparatus of claim 10, in which the first input circuit comprises a first buffer amplifier having a first input, a second input, and an output, wherein the first input of the buffer amplifier is coupled to the output of the buffer amplifier, second input of the buffer amplifier is coupled to the impedance circuit to receive a first constant impedance signal, and the output of the buffer amplifier is coupled to the input of the reference circuit.

13. The apparatus of claim 1, further comprising a second input circuit coupled between a second electrode and the input of the compensation circuit.

14. The apparatus of claim 13, in which the second input circuit comprises the impedance circuit coupled to the second input voltage, which comprises a second buffer amplifier having a first input, a second input, and an output, wherein the first input is coupled to the impedance circuit to receive second constant impedance signal, second input of the buffer amplifier is coupled to the output of the buffer amplifier, and the output of the buffer amplifier is coupled to the input of the compensation circuit.

15. The apparatus of claim 1, in which the reference circuit comprises:

an amplifier, having a first input, a second input, and an output, wherein the first input of the amplifier is coupled to the output of the amplifier, and the output of the amplifier is coupled to the first input of each of the first amplification circuit and the averager circuit;

a resistor, having first and second terminals, the first terminal of the resistor coupled to the second input of the amplifier and the second terminal of the resistor coupled to a ground voltage; and a capacitor, having first and second terminals, the first terminal of the capacitor coupled to the second input of the amplifier and the first terminal of the resistor, the second terminal of the capacitor coupled to the ground voltage.

16. The apparatus of claim 15, in which the reference circuit further comprises the impedance coupled to the first amplified input voltage, which comprises:

a resistor, having first and second terminals, the first terminal of the resistor coupled to the first input circuit, the second terminal is coupled to the first input of the amplifier; and a capacitor, having first and second terminals, the first terminal of the capacitor coupled to the first input circuit, the second terminal of the capacitor coupled to the first input of the amplifier.

17. The apparatus of claim 1, in which the compensation circuit comprises:

an amplifier, having a first input, a second input, and an output, wherein the first input of the amplifier is coupled to the output of the amplifier, and the output of the amplifier is coupled to the second input of each of the first amplification circuit and the averager circuit;

a resistor, having first and second terminals, the first terminal of the resistor coupled to the impedance circuit to receive a first control signal, the second terminal of the resistor coupled to the first input of the amplifier; and a capacitor, having a first and second terminal, the first terminal of the capacitor coupled to the effective impedance circuit to receive a second control signal, the second terminal of the capacitor coupled to the first input of the amplifier.

18. The apparatus of claim 17, in which the compensation circuit further comprises the impedance coupled to the second amplified input voltage, which comprises:

a resistor, having first and second terminals, the first terminal of the resistor coupled to the second input circuit, the second terminal is coupled to the first input of the amplifier; and a capacitor, having first and second terminals, the first terminal of the capacitor coupled to the second input circuit, the second terminal of the capacitor coupled to the first input of the amplifier.

19. An apparatus for sensing a difference between first and second input voltages, the apparatus comprises:

a first input circuit, providing a first buffered input voltage based on a signal received from a first electrode;

a second input circuit, providing a second buffered input voltage based on a signal received from a second electrode;

a reference circuit, providing a reference voltage signal based on the first buffered input voltage;

a compensation circuit, providing a compensated voltage signal based on the reference voltage signal;

a first amplification circuit, providing a differential output signal based on the reference and compensated voltage signals;

an averager circuit, providing a common mode (CM) output signal based on the reference and compensated input voltages; and an impedance circuit, approximately matching at least one of a gain/attenuation or a phase of the reference circuit and the first electrode to at least one of a respective gain/attenuation or a phase of the compensation circuit and the second electrode based on the differential and CM output signals.

20. The apparatus of claim 19, further comprising a phase-shifter receiving the CM output signal and providing a quadrature phase-shifted common mode (QCM) output signal, and wherein the impedance circuit includes a feedback controller circuit that comprises:

a first mixer, coupled to receive the differential and CM output signals, and providing a first mixer output based on the differential and the CM output signals; and a second mixer, coupled to receive the differential and QCM output signals, and providing a second mixer output based on the differential and the QCM output signals.

21. The apparatus of claim 20, in which the feedback controller circuit further comprises:

a first integrator, having an input coupled to the first mixer output, and providing a first control signal to control a component of an impedance in one of the compensation circuit and the impedance circuit; and a second integrator, having an input coupled to the second mixer output, and providing a second control signal to control a component of an impedance in one of the compensation circuit and the impedance circuit.

22. A method of detecting first and second input signals, the method comprising:

receiving the first input signal from a first electrode;

receiving the second input signal from a second electrode;

buffering the first input signal to circumvent a dominance of ECG cable capacitance over first input signal;

buffering the second input signal to circumvent the dominance of ECG cable capacitance over the second input signal;

obtaining a difference signal based on the first and second input signals;

obtaining a common mode (CM) signal based on the first and second input signals;

obtaining a quadrature common mode (QCM) signal that is phase-shifted from the CM signal; and approximately matching at least one of a gain/attenuation or a phase of the second input signal to at least one of a respective gain/attenuation or a phase of the first input signal, based on the difference between the CM and QCM signals.

23. The method of claim 22, in which matching the gain/attenuation or phase includes adjusting an impedance coupled to the second electrode based on an impedance coupled to the first electrode.

24. A system, comprising:

a first input circuit, providing a first input voltage based on a signal received from a first electrode;

a second input circuit, providing a second input voltage based on a signal received from a second electrode;

an amplification circuit, providing an electrocardiogram (ECG) output signal based on the first and second input voltages;

a right leg feedback electrode, operatively coupled to the amplification circuit to reduce common mode (CM) noise generated at the first and second electrodes; and a switch, operatively coupled between the amplification circuit and the right leg feedback electrode to selectively turn-off parasitic feedback coming from a right leg feedback electrode cable, when the right leg electrode is not being used.

25. The system of claim 24, wherein the system is an electrocardiogram (ECG) system.

26. The system of claim 24, wherein the first input circuit includes an impedance bootstrap circuit coupled between a first electrode and the amplification circuit.

27. The system of claim 24, wherein the second input circuit includes an impedance bootstrap circuit coupled between a second electrode and the amplification circuit.

28. The system of claim 24, wherein the amplification circuit, including a first input that is coupled to the first electrode to receive a first heart activity signal, a second input that is coupled to the second electrode to receive a second heart activity signal, and an output providing an electrocardiogram (ECG) output signal based on a difference between the first and second heart activity signals.

29. The system of claim 24, further includes a negative amplifier, operatively coupled between the switch and the amplification circuit to invert and amplify the common-mode noise signal.

30. A method of using an electrocardiogram (ECG) system, comprising:

receiving a first input signal from a first electrode;

receiving a second input signal from the second electrode;

disconnecting a right leg drive signal from a right leg ECG cable when a right leg feedback electrode is not being used;

obtaining a difference signal based on the first and second input signals; and displaying the difference signal as ECG output signal.

31. The method of claim 30, further includes:

determining to see if the right leg feedback electrode is being used to reduce common mode noise coming from the first and second electrodes; and disconnecting the right leg drive signal from the right leg ECG cable based on an outcome of the determination.

32. The method of claim 30, further includes:

sensing to see if the right leg feedback electrode is being used to reduce common mode noise coming from the first and second electrodes; and disconnecting the right leg drive signal from the right leg ECG cable based on an outcome of the sensing.

33. An apparatus for sensing a difference between first and second input voltages, comprising:

a first amplification circuit, including a first input receiving a signal based on a first input voltage, a second input receiving a signal based on a second input voltage, and an output providing a differential output signal based on a difference between the signals at the first and second inputs of the amplification circuit;

an averager circuit, including a first input receiving a signal based on the first input voltage, a second input receiving a signal based on the second input voltage, and an output providing a common mode (CM) output signal based on the signals at the first and second inputs to the averager circuit;

an automatic gain control circuit, including a first input receiving the common mode output signal from the averager circuit, and an output providing an amplitude regulated common mode signal;

a phase-shifter circuit, operatively coupled to the output of the automatic gain control circuit to receive the amplitude regulated CM output signal, and provide a quadrature common mode (QCM) output signal; and an impedance circuit, coupled to receive signals from the outputs of the first amplification and the phase-shifter circuits, where the impedance circuit adjusting an impedance, coupled to the second input voltage, based on the signals received from the outputs of the first amplification circuit and the phase-shifter circuit.

34. The apparatus of claim 33, in which the automatic gain control circuit further is comprises:

a voltage controlled amplifier (VCA), including a first input receiving a common mode output signal from the averager, a second input, and an output providing a controlled signal to a phase-shifter circuit;

an RMS-to-DC converter, including an input receiving the controlled signal from the VCA, and an output providing a direct current signal;

an amplifier, including a first input receiving the direct current signal from the RMS-to-DC converter, a second input receiving a reference voltage signal, and an output providing an amplitude regulated signal based on a difference between the reference and the direct current signals; and an integrator, including an input receiving the amplitude regulated signal from the amplifier and an output providing an integrated signal to the second input of the voltage controlled amplifier.

35. A method of detecting a voltage between first and second electrodes, the method comprising:

receiving a first input voltage from the first electrode;

receiving a second input voltage from the second electrode;

obtaining a difference signal based on the first and second input voltages;

obtaining a common mode (CM) signal based on the first and second input voltages where the CM signal includes a transient response time;

regulating amplitude of the CM signal such that the transient response time is essentially constant over input noise levels;

obtaining a quadrature common mode (QCM) signal that is phase shifted from the regulated CM signal;

multiplying components of the regulated common mode signal with the difference signal to provide a first control signal;

multiplying components of the difference signal with the components of the QCM signal to provide a second control signal; and matching at least one of a gain/attenuation or a phase of the first control signal to at least one of respective gain/attenuation or phase of the second control signal, based on a difference between regulated CM and QCM signals.

36. The method of claim 35, in which matching the gain/attenuation or phase includes adjusting an effective impedance coupled to the second electrode based on the first and second control signals and an impedance coupled to the first electrode.

37. A method of using an electrocardiogram to detect first and second input signals, the method comprising:

receiving the first input signal from a first electrode;

receiving the second input signal form a second electrode obtaining a difference signal based on the first and second input signals;

obtaining a common mode (CM) signal based on the first and second input signals;

regulating amplitude of the CM signal to keep a transient response time essentially constant for input noise levels;

obtaining a quadrature common mode (QCM) signal that is phase-shifted from the CM signal; and matching at least one of a gain/attenuation or a phase of the first input signal to at least one of respective gain/attenuation or phase of the first input signal, based on a difference between regulated CM and QCM signals.

38. The method of claim 37, in which matching the gain/attenuation or phase includes adjusting an impedance coupled to the second electrode based on an impedance coupled to the first electrode.

* * * * *

UNITED STATES PATENT AND TRADEMARK OFFICE
CERTIFICATE OF CORRECTION

PATENT NO.    : 6,496,721 B1
DATED         : December 17, 2002
INVENTOR(S)   : David J. Yonce It is certified that error appears in the above-identified patent and that said Letters Patent is hereby corrected as shown below:

Drawings,
Sheet 10, FIG. 8A, before "AT NODE 608", delete "SINGAL" and insert -- SIGNAL --, therefor.
Sheet 11, FIG. 8B, before "AT NODE 608", delete "SINGAL" and insert -- SIGNAL --, therefor.
Sheet 12, FIG. 9A, before "AT NODE 608", delete "SINGAL" and insert -- SIGNAL --, therefor.
Sheet 13, FIG. 9B, before "AT NODE 608", delete "SINGAL" and insert -- SIGNAL --, therefor.

Column 23,
Line 10, delete "is" after "further".

Signed and Sealed this

Eighth Day of April, 2003

JAMES E. ROGAN
*Director of the United States Patent and Trademark Office*